United States Patent [19]

Zurr et al.

[11] Patent Number: 5,648,235
[45] Date of Patent: Jul. 15, 1997

[54] METHOD AND MEANS FOR THE PRODUCTION OF GENE PRODUCTS, NOVEL RECOMBINANT DNA VECTORS THEREFOR AND KITS EMPLOYING THEM

[75] Inventors: Daniel Zurr, Herzliya; Zehava Grossman, Rehovot; Yaron Nophar, Ramat-gan, all of Israel

[73] Assignee: Q.B.I. Enterprises Ltd., Omer, Israel

[21] Appl. No.: 399,580

[22] Filed: Mar. 8, 1995

Related U.S. Application Data

[63] Continuation-in-part of Ser. No. 84,893, Jun. 29, 1993, abandoned.

[30] Foreign Application Priority Data

Jul. 3, 1992 [IL] Israel ........................................ 102404

[51] Int. Cl.$^6$ ............................ C12P 21/06; C12N 15/63; C12N 5/06; C07H 21/04
[52] U.S. Cl. ................... 435/69.1; 435/91.33; 435/172.3; 435/320.1; 435/360; 435/325; 536/23.1; 536/23.2; 536/23.72
[58] Field of Search ............................. 435/69.1, 91.33, 435/172.3, 240.2, 320.1; 536/23.1, 23.2, 23.72

[56] References Cited

U.S. PATENT DOCUMENTS 5,358,856 10/1994 Baltimore et al. .................... 435/69.1

FOREIGN PATENT DOCUMENTS

| 0585983A2 | 3/1994 | European Pat. Off. . |
| 4206769A1 | 9/1993 | Germany . |
| WO90/01550 | 2/1990 | WIPO . |
| WO91/00905 | 1/1991 | WIPO . |
| WO93/11250 | 6/1993 | WIPO . |

OTHER PUBLICATIONS

Davies, M.V. et al., The Journal of Biological Chemistry, "The Effect of Poliovirus Proteinase 2A$^{pro}$ Expression on Cellular Metabolism", pp. 14714–14720, Aug. 5, 1991.

"The Effect of Poliovirus Proteinase 2A$^{pro}$ Expression on Cellular Metabolism", The Journal of Biological Chemistry, pp. 14714–14720, Aug. 5, 1991.

Jang et al., "Cap–Independent Translation of Picornavirus RNAs: Structure and Function of the Internal Ribosomal Entry Site", Enzyme 44:292–309 (1990) (no month available on the reference).

Macejak et al., "Translation Regulation of the Immunoglobulin Heavy–Chain Binding Protein mRNA", Enzyme, 44:310–329 (1990) (no month available on the reference).

Weighous et al., "A Bacteriophage Transcription Terminator Permits the Cloning of a Mammalian Expression Vector Carrying the Human Preprorenin Gene in E. coli", Biochem. Biophys. Rec. Commun., 143:593–599 (Mar. 1987).

Zhou et al., "Synthesis of Functional mRNA in Mammalian Cells by Bacteriophage T3 RNA Polymerase", Mol. Cell. Biol., 10:4529–4539 (Sep. 1990).

Alvey et al., "cis–and trans–Cleavage Activities of Poliovirus 2A Protease Expressed in Escherichia coli", Journal of Virology, 65(11):6077–6083 (Nov. 1991).

Bonneau et al, "Involvement of the 24–kDa Cap–binding Protein in Regulation of Protein Synthesis in Mitosis", Journal of Biological Chemistry, 262(23):11134–11139 (Aug. 15, 1987).

Duke et al., "Sequence and Structural Elements That Contribute to Efficient Encephalomyocarditis Virus RNA Translation", Journal of Virology, 66(3):1602–1609 (Mar. 1992).

Gorman et al., "Recombinant Genomes Which Express Chloramphenicol Acetyltransferase in Mammalian Cells", Molecular and Cellular Biology, 2(9):1044–1051 (Sep. 1982).

Karlsson et al., "A mutational analysis of the insulin gene transcription control region: Expression in beta cells is dependent on two related sequences within the enhancer", Proc. Nat. Acad. Sci., 84:8819–8823 (Dec. 1987).

Miyazawa et al., "Molecular Cloning and Sequence Analysis of cDNA For Human Hepatocyte Growth Factor", Biochemical and Biophysical Research Communications, 163(2):967–973 (Sep. 15, 1989).

Nyborg et al., "Interaction of Host Cell Proteins with the Human T–cell Leukemia Virus Type I Transcriptional Control Region", Journal of Biological Chemistry, 265(14):8237–8242 (May 15, 1990).

Racaniello et al, "Molecular Cloning of Poliovirus cDNA and Determination of the Complete Nucleotide Sequence of the Viral Genome", Proc. Natl. Acad. Sci., 78(8):4887–4891 (Aug. 1981).

Toyoda et al., "A Second Virus–Encoded Proteinase Involved in Proteolytic Processing of Poliovirus Polyprotein", Cell, 45:761–770 (Jun. 6, 1986).

deWet et al., "Firefly Luciferase Gene: Structure and Expression in Mammalian Cells", Molecular and Cellular Biology, 7:725–737 (Feb. 1987).

La Monica et al., "Mapping of Sequences Required for Mouse Neurovirulence of Poliovirus Type 2 Lansing", Journal of Virology, 57:515–525 (Feb. 1986).

Ellman et al., "A New and Rapid Colorimetric Determination of Acetylcholinesterase Activity", Biochemical Pharmacology, 7:88–95 (Jul 1961).

DeFeo et al., "Analysis of two divergent rat genomic clones homologous to the transforming gene of Harvey murine sarcoma virus", Proc. Natl. Acad. Sci., 78:3328–3332 (Jun. 1981).

(List continued on next page.)

Primary Examiner—Douglas W. Robinson
Assistant Examiner—Thanda Wai
Attorney, Agent, or Firm—Merchant, Gould, Smith, Edell, Welter & Schmidt, P.A.

[57] ABSTRACT

An effective method for the production of a gene product employs recombinant DNA vectors comprising a gene encoding a TIF of a eukaryotic translation factor preceeded by a weak eukaryotic promoter, and at least one internal ribosomal entry site region followed by a gene encoding a desired gene product.

45 Claims, 12 Drawing Sheets

OTHER PUBLICATIONS

Laemmli, "Cleavage of Structural Proteins during the Assembly of the Head of Bacteriophage T4", *Nature*, 227:680 (Aug. 15, 1970).

Jang et al., Enzyme, 44:292–309 (1990).

Macejak et al., Enzyme, 44:310–329 (1990).

Weighous et al., Biochem. Biophys. Res. Commun; 143:593–599 (Mar. 1987).

Zhou et al. Mol. Cell. Biol., 10:4529–4539 (Sep. 1990).

o = transfection 1
△ = transfection 2
X = transfection 3
● = transfection 4

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
        ( A ) LENGTH: 223 base pairs
        ( B ) TYPE: nucleic acid
        ( C ) STRANDEDNESS: double
        ( D ) TOPOLOGY: unknown ( i i ) MOLECULE TYPE: cDNA ( x i ) SEQUENCE DESCRIPTION: SEQ ID NO:1:

```
CTGCAGCACG  TGCACGTGCA  CGTGCACGTG  TCGACTCTAG  AGGATCCGGC  CCCGCCCAGC      60

GTCTTGTCAT  TGGCGAATTC  GAACACGCAG  ATGCAGTCGG  GGCGGCGCGG  TCCGAGGTCC     120

ACTTCGCATA  TTAAGGTGAC  GCGTGTGGCC  TCGAACACCG  AGCGACCCTG  CAGCGACCCG     180

CTTAACAGCG  TCAACAGCGT  GCCGCAGATC  TCGAGGAGCT  TGG                        223
```

( 2 ) INFORMATION FOR SEQ ID NO:2:

( i ) SEQUENCE CHARACTERISTICS:
        ( A ) LENGTH: 450 base pairs
        ( B ) TYPE: nucleic acid
        ( C ) STRANDEDNESS: double
        ( D ) TOPOLOGY: unknown ( i i ) MOLECULE TYPE: cDNA ( x i ) SEQUENCE DESCRIPTION: SEQ ID NO:2:

| | | | | | |
|---|---|---|---|---|---|
| CCTGGGGACA | GGGGTCCTGG | GGACAGGGGT | CTGGGGACAG | CAGCGCAAAG | AGCCCCGCCC | 60
| TGCAGCCTCC | AGCTCTCCTG | GTCTAATGTG | GAAAGTGGCC | CAGGTGAGGG | CTTTGCTCTC | 120
| CTGGAGACAT | TTGCCCCAG | CTGTGAGCAG | GGACAGGTCT | GGCCACCGGG | CCCCTGGTTA | 180
| AGACTCTAAT | GACCCGCTGG | TCCTGAGGAA | GAGGTGCTGA | CGACCAAGGA | GATCTTCCCA | 240
| CAGACCCAGC | ACCAGGGAAA | TGGTCCGGAA | ATTGCAGCCT | CAGCCCCAG | CCATCTGCCG | 300
| ACCCCCCAC | CCCAGGCCCT | AATGGGCCAG | GCGGCAGGGG | TTGACAGGTA | GGGGAGATGG | 360
| GCTCTGAGAC | TATAAAGCCA | GCGGGGGCCC | AGCAGCCCTC | AGCCCTCCAG | GACAGGCTGC | 420
| ATCAGAAGAG | GCCATCAAGC | AGGTCTGTTC | | | | 450

( 2 ) INFORMATION FOR SEQ ID NO:3:

( i ) SEQUENCE CHARACTERISTICS:
( A ) LENGTH: 480 base pairs
( B ) TYPE: nucleic acid
( C ) STRANDEDNESS: double
( D ) TOPOLOGY: unknown ( i i ) MOLECULE TYPE: cDNA ( x i ) SEQUENCE DESCRIPTION: SEQ ID NO:3:

| | | | | | |
|---|---|---|---|---|---|
| TCTAGAGGAT | CCAGATGGGA | TTCGGACACC | AAAACAAAGC | GGTGTACACT | GCAGGTTACA | 60
| AAATTTGCAA | CTACCATTTG | GCCACTCAGG | AAGATTTGCA | AAACGCAGTG | AACGTCATGT | 120
| GGAATAGAGA | CCTCTTAGTC | ACAGAATCAA | GAGCCCAGGG | CACCGATTCA | ATCGCAAGGT | 180
| GCAATTGCAA | CGCAGGGGTG | TACTACTGCG | AGTCTAGAAG | GAAATACTAC | CCAGTATCCT | 240
| TCGTTGGCCC | AACGTTCCAG | TACATGGAGG | CTAATAACTA | TTACCCAGCT | AGGTACCAGT | 300
| CCCATATGCT | CATTGGCCAT | GGATTCGCAT | CTCCAGGGGA | TTGTGGTGGC | ATACTCAGAT | 360
| GTCACCACGG | GGTGATAGGG | ATCATTACTG | CTGGTGGAGA | AGGGTTGGTT | GCATTTACAG | 420
| ACATTAGAGA | CTTGTATGCC | TACGAAGAAG | AAGCCATGGA | ACAATAATAA | GCTTCGTATG | 480

( 2 ) INFORMATION FOR SEQ ID NO:4:

( i ) SEQUENCE CHARACTERISTICS:
( A ) LENGTH: 527 base pairs
( B ) TYPE: nucleic acid
( C ) STRANDEDNESS: double
( D ) TOPOLOGY: unknown ( i i ) MOLECULE TYPE: cDNA ( x i ) SEQUENCE DESCRIPTION: SEQ ID NO:4:

| | | | | | |
|---|---|---|---|---|---|
| CCGGATCCGT | TATTTTCCAC | CATATTGCCG | TCTTTTGGCA | ATGTGAGGGC | CCGGAAACCT | 60
| GGCCCTGTCT | TCTTGACGAG | CATTCCTAGG | GGTCTTTCCC | CTCTCGCCAA | AGGAATGCAA | 120
| GGTCTGTTGA | ATGTCGTGAA | GGAAGCAGTT | CCTCTGGAAG | CTTCTTGAAG | ACAAACAACG | 180
| TCTGTAGCGA | CCCTTTGCAG | GCAGCGGAAC | CCCCCACCTG | GCGACAGGTG | CCTCTGCGGC | 240
| CAAAAGCCAC | GTGTATAAGA | TACACCTGCA | AAGGCGGCAC | AACCCCAGTG | CCACGTTGTG | 300
| AGTTGGATAG | TTGTGGAAAG | AGTCAAATGG | CTCTCCTCAA | GCGTATTCAA | CAAGGGGCTG | 360
| AAGGATGCCC | AGAAGGTACC | CCATTGTATG | GGATCTGATC | TGGGGCCTCG | GTGCACATGC | 420
| TTTACATGTG | TTTAGTCGAG | GTTAAAAAAC | GTCTAGGCCC | CCGAACCAC | GGGGACGTGG | 480
| TTTTCCTTTG | AAAAACACGA | TGATAATACC | ATGTGGGTGA | CCAAACT | | 527

( 2 ) INFORMATION FOR SEQ ID NO:5:

( i ) SEQUENCE CHARACTERISTICS:
    ( A ) LENGTH: 245 base pairs
    ( B ) TYPE: nucleic acid
    ( C ) STRANDEDNESS: double
    ( D ) TOPOLOGY: unknown ( i i ) MOLECULE TYPE: cDNA ( x i ) SEQUENCE DESCRIPTION: SEQ ID NO:5:

```
ACATCGGAAT TCAGGTCGAC GCCGGCCAAG ACAGCACAGA CAGATTGACC TATTGGGGTG      60
TTTCGCGAGT GTGAGAGGGA AGCGCCGCGG CCTGTATTTC TAGACCTGCC CTTCGCCTGG     120
TTCGTGGCGC CTTGTGACCC CGGGCCCCTG CCGCCTGCAA GTCGAAATTG CGCTGTGCTC     180
CTGTGCTACG GCCTGTGGCT GGACTGCCTG CTGCTGCCCA ACTGGCTGGC AAGAAGCTTC     240
GTATG                                                                 245
```

( 2 ) INFORMATION FOR SEQ ID NO:6:

( i ) SEQUENCE CHARACTERISTICS:
        ( A ) LENGTH: 35 base pairs
        ( B ) TYPE: nucleic acid
        ( C ) STRANDEDNESS: double
        ( D ) TOPOLOGY: unknown ( i i ) MOLECULE TYPE: cDNA ( x i ) SEQUENCE DESCRIPTION: SEQ ID NO:6:

```
AACATCGCGG CCGCAGGTCG ACGCCGGCCA AGACA                                 35
```

( 2 ) INFORMATION FOR SEQ ID NO:7:

( i ) SEQUENCE CHARACTERISTICS:
        ( A ) LENGTH: 33 base pairs
        ( B ) TYPE: nucleic acid
        ( C ) STRANDEDNESS: double
        ( D ) TOPOLOGY: unknown ( i i ) MOLECULE TYPE: cDNA ( x i ) SEQUENCE DESCRIPTION: SEQ ID NO:7:

```
CATACGAAGC TTCTTGCCAG CCAGTTCGGC AGC                                   33
```

( 2 ) INFORMATION FOR SEQ ID NO:8:

( i ) SEQUENCE CHARACTERISTICS:
        ( A ) LENGTH: 18 base pairs
        ( B ) TYPE: nucleic acid
        ( C ) STRANDEDNESS: double
        ( D ) TOPOLOGY: unknown ( i i ) MOLECULE TYPE: cDNA ( x i ) SEQUENCE DESCRIPTION: SEQ ID NO:8:

```
ATTTGCTGGG TGAATCCA                                                    18
```

( 2 ) INFORMATION FOR SEQ ID NO:9:

( i ) SEQUENCE CHARACTERISTICS:
        ( A ) LENGTH: 33 base pairs
        ( B ) TYPE: nucleic acid
        ( C ) STRANDEDNESS: double
        ( D ) TOPOLOGY: unknown ( i i ) MOLECULE TYPE: cDNA ( x i ) SEQUENCE DESCRIPTION: SEQ ID NO:9:

```
TCCAACAAGC TTATGGGTTT TGGCCACCAA AAT                                   33
```

( 2 ) INFORMATION FOR SEQ ID NO:10:

( i ) SEQUENCE CHARACTERISTICS:
    ( A ) LENGTH: 38 base pairs
    ( B ) TYPE: nucleic acid
    ( C ) STRANDEDNESS: double
    ( D ) TOPOLOGY: unknown ( i i ) MOLECULE TYPE: cDNA ( x i ) SEQUENCE DESCRIPTION: SEQ ID NO:10:

CCTATCGCGG CCGCTTATTA CTGCTCCATA GCCTCCTC      38

( 2 ) INFORMATION FOR SEQ ID NO:11:

( i ) SEQUENCE CHARACTERISTICS:
    ( A ) LENGTH: 30 base pairs
    ( B ) TYPE: nucleic acid
    ( C ) STRANDEDNESS: double
    ( D ) TOPOLOGY: unknown ( i i ) MOLECULE TYPE: cDNA ( x i ) SEQUENCE DESCRIPTION: SEQ ID NO:11:

ACCATTCGCG ACACGGCGGA GGCGCACGGC      30

( 2 ) INFORMATION FOR SEQ ID NO:12:

( i ) SEQUENCE CHARACTERISTICS:
    ( A ) LENGTH: 34 base pairs
    ( B ) TYPE: nucleic acid
    ( C ) STRANDEDNESS: double
    ( D ) TOPOLOGY: unknown ( i i ) MOLECULE TYPE: cDNA ( x i ) SEQUENCE DESCRIPTION: SEQ ID NO:12:

CCTAGGAAGC TTGATCATGG CGAGCTGAAG AGGC      34

( 2 ) INFORMATION FOR SEQ ID NO:13:

( i ) SEQUENCE CHARACTERISTICS:
    ( A ) LENGTH: 35 base pairs
    ( B ) TYPE: nucleic acid
    ( C ) STRANDEDNESS: double
    ( D ) TOPOLOGY: unknown ( i i ) MOLECULE TYPE: cDNA ( x i ) SEQUENCE DESCRIPTION: SEQ ID NO:13:

TCTAGAGGAT CCAGATGGGA TTCGGACACC AAAAC      35

( 2 ) INFORMATION FOR SEQ ID NO:14:

( i ) SEQUENCE CHARACTERISTICS:
    ( A ) LENGTH: 33 base pairs
    ( B ) TYPE: nucleic acid
    ( C ) STRANDEDNESS: double
    ( D ) TOPOLOGY: unknown ( i i ) MOLECULE TYPE: cDNA ( x i ) SEQUENCE DESCRIPTION: SEQ ID NO:14:

CATACGAAGC TTATTATTGT TCCATGGCTT CTT      33

( 2 ) INFORMATION FOR SEQ ID NO:15:

( i ) SEQUENCE CHARACTERISTICS:

(A) LENGTH: 39 base pairs
        (B) TYPE: nucleic acid
        (C) STRANDEDNESS: double
        (D) TOPOLOGY: unknown (ii) MOLECULE TYPE: cDNA (xi) SEQUENCE DESCRIPTION: SEQ ID NO:15:

CACAGCGGCC GCGGATCCGT TATTTCCAC CATATTGCC      39

(2) INFORMATION FOR SEQ ID NO:16:

(i) SEQUENCE CHARACTERISTICS:
        (A) LENGTH: 39 base pairs
        (B) TYPE: nucleic acid
        (C) STRANDEDNESS: double
        (D) TOPOLOGY: unknown (ii) MOLECULE TYPE: cDNA (xi) SEQUENCE DESCRIPTION: SEQ ID NO:16:

AGTTGGTCA CCCACATGGT ATTATCATCG TGTTTTCA      39

METHOD AND MEANS FOR THE PRODUCTION OF GENE PRODUCTS, NOVEL RECOMBINANT DNA VECTORS THEREFOR AND KITS EMPLOYING THEM

This application is a continuation in part of U.S. application Ser. No. 08/084,893 filed on Jun. 29, 1993, now abandoned. U.S. application Ser. No. 08/084,893 is incorporated herein by reference.

FIELD OF THE INVENTION

The present invention relates to the synthesis of gene product. More particularly, the invention relates to a novel method for producing gone products, such as polypeptides and proteins, in eukaryotic cells with high yield, to novel recombinant vectors therefor, to products obtained thereby, to their use, and to kits directed to the increased production of said proteins.

BACKGROUND OF THE INVENTION

The production of various proteins and peptides with commercial value is the basis for the establishment and the rapid growth of the genetic engineering industry. This is facilitated by utilizing sophisticated recombinant DNA technologies rather than conventional synthetic routes used by the chemical industry, which are inapplicable. At the core of these technologies is the in vitro fermentation of microorganisms, typically a bacteria, containing the fight gene (in an appropriate expression vector) encoding the target protein. The fermentation is followed by "harvesting" the genetically engineered microorganisms and isolating the desired product through a series of separation and purification processes.

This method has some drawbacks. (a) Eukaryotic proteins expressed in microorganisms are often not properly folded; in particular, glycosylation and the proper conformation of complex proteins are not performed correctly. (b) Proteins expressed in large amounts often precipitate into insoluble aggregates (inclusion bodies) from which they can be recovered only by solubilization in denaturing agents. (c) Proteins which are secreted into the periplasmic space of the producer cell when produced in small amounts, often cannot be secreted there when produced in large amounts.

Compared with the above-mentioned bacterial systems, mammalian expression techniques have certain advantages, particularly for the expression of higher eukaryotic proteins. The expressed proteins are usually properly modified, and they almost always accumulate in the correct cellular compartment. So far, however, the mammalian expression techniques are practical for small and medium-scale work, but they are difficult and very expensive to perform on an industrial scale.

In eukaryotic organisms the synthesis of proteins is mediated by the ribosome scanning model. The (40S) ribosomal sub-unit (carrying Met-tRNA and various initiation factors) binds at the 5' end of the mRNA and then migrates in a 5'–3' direction, stopping at the first AUG codon in favorable context for initiating translation.

In eukaryotes, most cellular cytoplasmic mRNA's carry a 7-methylguanylate cap attached to their 5' end. The binding of the ribosomal sub-unit near or at the 5' end of the mRNA is facilitated by an interaction between the methylated cap structure and the cap binding protein complex. This complex includes a eukaryotic translation-initiation factor eIF-4F (which contains the subunit p220).

Picornaviruses are mammalian and plant plus strand RNA viruses whose genomes serve as mRNAs. These viruses are capable of blocking translation of cellular mRNA without affecting translation of vital mRNA. The mechanism of this shut-off is related to inactivation of the eukaryotic translation initiation factor eIF-4F. Poliovirus (RNA+stranded picornavirus), induces the cleavage of the P220 (eIF-4F) and thus prevents the binding of capped mRNA to the 40S ribosome as part of the translation initiation process. The cleavage of the P220 component is done directly or indirectly by the poliovirus protease 2A, a translation inhibition factor (TIF). 2A is a protease, the mature form of which is generated by the cleavage of the precursor polyprotein of poliovirus at its N terminus by 2A itself and at its C terminus by another protease 3C [F. Toyoda et al., 1988, Cell 45, pp. 761–770]. The vital strategy therefore prevents cap dependent translation of cellular mRNA's, without affecting the cap independent translation of vital mRNA. A large segment of the viral 5' untranslated region (UTR), approximately 750 nucleotides in length, promotes "internal" entry of ribosomes without the need for 5' capping of the mRNA. Vital mRNA is therefore translated by a mechanism in which the ribosome binds directly to an internal site of the mRNA without any need for p220. Thus Picornaviruses cause a dramatic shut-off of host cell mRNA translation (within several hours after infection), while allowing the cap independent translation of vital mRNA.

It is known that few cellular mRNAs, such as the one encoding the immunoglobulin heavy chain binding protein (BiP) can be translated in poliovirus-infected cells at a time when cap dependent translation of all other host cell mRNA is inhibited. The 5' leader of BiP (UTR), like that of poliovirus, can directly confer internal ribosome binding to an mRNA in mammalian cells.

Zhou et. al. (Molecular and Cellular Biology, 1990, 10, 4529–4539) transiently co-transfect a cell line with a vector in which an internal ribosome entry site (IRES) precedes a reporter gene, and another vector in which an internal ribosome entry site (IRES) precedes the poliovirus 2A gene. These transfected cells express 2A for a limited period of time and allow only for transient expression of the reporter gene. Production of most proteins needed for cellular viability is arrested because translation of all capped mRNA is blocked, thus leading to cell death.

It is common knowledge that expression of 2A in cells can only be transient, due to cellular death. In a patent application of the same applicant herein (EP 585,983) expression systems permitting constitutive expression of the 2A protease in stable eukaryotic cell lines have been described. It is an object of the present invention to provide improved vectors which can be used in the expression systems of EP 585,983.

The following terms as used herein have the indicated meanings:

BiP—The human immunoglobuhn heavy chain-binding protein (also known as GRP 78).

ETF—Eukaryotic translation Factor, e.g., the eIF-4F complex.

Eukaryotic Promoter—A DNA fragment that precedes a gene and enhances its transcription in eukaryotic cells.

Gene Product—a translation product, comprising—but not limited to—polypeptides and proteins.

In vitro production—the production of one or more selected polypeptides in eukaryotic cell lines.

IRES—Internal ribosome entry site.

Polyfunctional cloning site—A DNA sequence that contains restriction sites for two or more restriction enzymes, and into which various genes can be cloned.

Recombinant Nucleotide Vector—A vector including a recombinant nucleotide sequence.

TIF—Eukaryotic translation inhibition factor, e.g. the poliovirus protease 2A.

Transfection—The introduction of a vector containing a recombinant nucleotide sequence (DNA or an RNA) encoding one or more genes to be expressed into a host cell.

UTR—an IRES containing the 5' untranslated region of picornavirus or of BiP.

Vector—Any autonomously replicating or integrating agent, including but not limited to, plasmids, viruses, phages and the like.

Vector system—The ensemble of two or more vectors which cooperate in the production of a gene product.

Weak eukaryotic promoter—A eukaryotic promoter that precedes a TIF gene and allows its constitutive expression in stable eukaryotic cell lines.

SUMMARY OF THE INVENTION

It is therefore clear that it is highly desirable to be able to provide a method by means of which production of gene products in eukaryotic cells could be carried out on an industrial scale and in an economic manner.

It is an object of the present invention to provide such a method which overcomes the limitations so far inherent to gene products production in eukaryotic cells.

It is another object of the invention to provide methods and recombinant nucleotide vectors which can be employed for this purpose.

It is still another object of the invention to provide methods by means of which cell activity can be controlled, under production conditions.

The method for production of desired proteins, uses an "on-off translation mechanism". The desired gene is preceded by an IRES, while the TIF is preceded by a eukaryotic promoter with a cap-dependent translation initiation. After transfection and subsequent expression of the TIF in the cells, ETF is inactivated. As a consequence, capped cellular mRNA is unable to associate with the ribosomes, while the translation initiation by the internal ribosome entry site binding mechanism of the selected protein mRNA continues, as it is independent of the ETF.

Since the TIF is translated via a cap-dependent mechanism, as soon as the amount of TIF increases in the cell, its production is depleted due to a slowdown in its translation. The cells then switches back, temporarily, to normal activity, allowing for the recovery of metabolic processes necessary to ensure cellular viability. The production of the TIF is then also restored, starting the whole cycle again.

It has now further been found that the "on-off translation mechanism" can be better exploited to obtain gene products in significant amounts by constructing improved vectors based on capped 2A translation, that induce constitutive expression of a TIF in a stable cell line. These vectors include a TIF which is preceded by a weak eukaryotic promoter, limiting its transcription and thus allowing for the formation of stable transfected cell lines that constitutively express low levels of TIF. This expression partially inhibits translation of capped cellular mRNA and selectively increases production of selected genes of interest, which genes are preceded by an IRES.

It is therefore also an object of the present invention to provide recombinant nucleotide vector(s) by means of which a TIF could be constitutively expressed in eukaryotic cells.

It is still another object of the invention to provide stable cell lines comprising said recombinant nucleotide vector(s) and expressing said TIF constitutively.

It is another object of the invention to use the abovementioned vector(s) and cell lines for the increased production of desired gene products.

It is yet another object of the invention to provide kits for the improved production of gene products, which incorporate the vectors and cell lines of the invention and which can be used to express desired genes.

It should be understood that whenever the terms "gene product" or "polypeptide" or "protein" are used, they are meant to be used interchangeably, mutatis mutandis.

The present invention is directed, inter alia, to methods and vectors by means of which the cap-dependent translation of cell proteins is inhibited while allowing the cap-independent translation of engineered gene products to proceed.

DETAILED DESCRIPTION OF THE INVENTION

Generally speaking, the method for the in vitro production of a gene product, according to the invention, comprises the steps of:

a) preparing one or more recombinant nucleotide vector(s) capable of eukaryotic cell transfection, collectively containing 1) a gene encoding a TIF of an eukaryotic translation factor (ETF), preceeded by a cap-dependent promoter, 2) at least one internal ribosome entry site (IRES) region, and 3) at least one gene encoding a polypeptide which it is desired to produce;

b) transfecting a eukaryotic cell culture with the said vector;

c) keeping the transfected cell culture under conditions suitable to promote cell activity; and d) recovering the desired gene product from the said culture.

According to one embodiment of the invention the ETF comprises, or essentially consists of, the eIF-4F complex.

According to another embodiment of the invention, the recombinant nucleotide vector can be a DNA or an RNA vector.

In one embodiment of the invention, the recombinant nucleotide vector comprises, in the same vector, 1) a sequence encoding a TIF preceded by a eukaryotic cap-dependent promoter; and 2) a sequence encoding the desired gene product preceded by an IRES.

Preferably, but non-limitatively, the gene encoding the TIF is the cDNA of the poliovirus 2A protease and the IRES region is that of a picornavirus or of BiP (UTR).

The method for the in vitro production of a gene product according to the invention, comprises the steps of:

a) preparing a first recombinant nucleotide vector, comprising a sequence encoding a TIF, preceded by a eukaryotic cap-dependent promoter;

b) preparing a second recombinant nucleotide vector, comprising at least a sequence encoding the desired gene product, preceded by an IRES;

c) transfecting a eukaryotic cell culture with both the said first vector and the said second vector;

d) keeping the transfected cell culture under conditions suitable to promote cell activity; and e) recovering the desired gene product from the said culture.

As stated, the gene product can be any useful material, e.g., a polypeptide or a protein.

Of course, as will be further explained hereinafter, the TIF activity and the gene expression, preceded by an IRES, can be split between two or more different vectors which are all introduced into the cell. Such a separation of functions between separate vectors is substantially equivalent to their inclusion in a single vector and, as such, also forms a part of the present invention.

It should be understood that, according to the invention, while expression of the polypeptide of choice is obtained in all cases by preceding the gene which codes for it with an IRES the TIF is preceeded by a weak eukaryotic promoter. Shut off of cell activities will lead also to the stoppage of TIF translation, thus allowing a periodic recovery of normal cell activities which prolongs the life of the cell.

As will be apparent to the skilled person, a great variety of genes encoding TIFs and IRESes as well as of proteins to be expressed, can be provided without exceeding the scope of the invention, and all recombinant nucleotide vectors which contain, a gene encoding a TIF, a weak eukaryotic promoter, an IRES and a gene encoding a polypeptide to be produced, are encompassed by the present invention.

Representative but non-limitative examples of such genes and sequences, as further more fully detailed hereinafter, include the IRES region of a picornavirus or of BiP, and the cDNA of the poliovirus 2A protease. Of course, non-functional sequences can be present between the various genes, as they are not out of the scope of the invention, and the term "sequential" is to be read in respect of functional sequences only.

Picornaviruses are mammalian plus strand RNA viruses whose genomes serve as mRNA. A large segment of the 5' non-translated region (UTR), approximately 400 nucleotides in length, promotes "internal" entry of ribosomes independent of the non-capped 5' end of the mRNA. Thus the vital mRNA is translated by a mechanism in which the ribosome binds directly to an internal site of the mRNA.

Poliovirus is RNA+stranded picornavirus whose polyprotein, encoded by an open reading frame spanning most of the vital RNA, is processed by the virus encoded proteases (a TIF). Picornaviruses cause a dramatic shut-off of host cell mRNA translation (within several hours after infection).

The mechanism of shut-off is related to inactivation of the eukaryotic translation initiation factor eIF-4F (an ETF). Poliovirus induces the cleavage of the P220 component of eIF-4F a factor that assists the binding of capped mRNA to the 40S ribosome as part of the translation initiation process. The cleavage of the P220 component is caused by the poliovirus protease 2A (a TIF). The virus strategy thus appears to be to prevent the cap dependent translation initiation used by cellular mRNAs, while allowing the cap independent internal translation of polio viral RNA.

Poliovirus 2A is a protease the mature form of which is generated by the cleavage of the precursor polyprotein of poliovirus at its N terminus by 2A itself and at C terminus by another protease 3C [Fl. Toyoda et al., 1988, Cell 45, pp. 761–770].

It is known that a cellular mRNA, encoding the immunoglobulin heavy chain binding protein (BiP) can be translated in poliovirus-infected cells at a time when cap dependent translation of all host cell mRNA is inhibited. The 5' leader of BiP (UTR) can directly confer internal ribosome binding to an mRNA in mammalian cells.

As will be further apparent to the skilled person, the invention can also be employed for gene therapy, in vivo, in a therapeutic method which requires increased protein production in protein-deficient cells. Of course, it is also possible to produce a material which will ultimately cause cell death. This is useful, for instance, in cancer therapy. The produced material may be, e.g., a toxin or 2A protease, or any other suitable material which will eventually cause cell death. Thus an appropriate vector can be constructed, which contains the desired gene encoding the required protein, preceded by an IRES, which can be used in an appropriate pharmaceutical preparation in the transfection of cells of a patient in need thereof. Of course, any such vector and pharmaceutical preparations also form a part of the present invention.

It is also known to persons skilled in the art to target a specific vector to be transfected solely or principally into a specific type of cells. This, of course, is useful for a variety of therapeutic treatments employing the methods and vectors of the invention.

Also encompassed by the present invention is the extracellular production of a polypeptide, by employing an appropriate mRNA construct in a medium which mimicks cell conditions necessary for the translation of an IRES-preceded gene.

Thus, in one aspect, the invention is directed to a method for the extracellular production of a gene product, which method comprises the steps of:

a) preparing a medium containing a recombinant nucleotide vector comprising at least one sequence encoding the desired gene product, preceded by an IRES;

b) providing in the medium substrates, ribosomes and promotors required for effecting translation;

c) keeping the medium under conditions suitable to promote gene expression; and d) recovering the desired gene product from the said medium.

The present invention is directed, inter alia, to vectors which can stably transfect eukaryotic cells and induce constitutive expression of a TIF in the transfected cells without causing cell death. Such constitutive, non-lethal expression of a TIF leads to inhibition of most of the cap-dependent translation of cell proteins while allowing the cap-independent translation of engineered gene products to proceed. A minimal amount of cap-dependent translation that is essential for cellular viability is maintained, by limiting transcription and translation of the TIF. This is done by preceding the TIF gene with a weak eukaryotic promoter that minimizes its transcription, and by ensuring the TIF is translated in a cap-dependent manner.

Generally speaking, according to the invention, the recombinant vector or vector system comprises a gene encoding a TIF of a eukaryotic translation factor (ETF), preceded by a promoter, wherein the promoter is a weak eukaryotic promoter, and at least one gene encoding a polypeptide which it is desired to produce, preceded by at least one internal ribosome entry site (IRES) region.

The invention is also directed to a cell line, stably transfected with the abovementioned vector or vector system, wherein said cell line constitutively expresses a TIF.

A weak promoter in the context of the present invention is a promoter which permits to create stable cell-lines in which a TIF, such as the poliovirus 2A protease, is constitutively expressed in its active form. Specifically cells are transformed with a construct bearing the 2A protease, and stable transfected cell lines are established three weeks after transfection. Presence and activity of the TIF are determined by a functional assay such as the cleavage assay for the 2A protease, described by Alvey et al. (Alvey, S. K. et al., J. Virol. 65, 6077–6083 (1991)).

Illustrative but non-limitative examples of weak eukaryotic promoters are the Mini TK (SEQ. ID NO. 1) or the insulin promoters (SEQ. ID NO. 2).

According to a preferred embodiment of the invention, the ETF comprises, or essentially consists of, the endogenous eIF-4F complex. According to another preferred embodiment of the invention the gene encoding the TIF is the cDNA of the poliovirus 2A protease (SEQ. ID NO. 3). In still another preferred embodiment of the invention the IRES region is the UTR of EMCV (SEQ. ID NO. 4) or of BiP (SEQ. ID NO. 5).

In one embodiment of the invention, a single recombinant nucleotide vector comprises a sequence encoding a TIF preceded by a weak eukaryotic promoter, and the desired gene product preceded by an IRES.

According to this embodiment, the invention is directed to a method of producing a gene product, said method comprising the steps of:

a) preparing a recombinant nucleotide vector, comprising a sequence encoding a TIF preceded by a weak eukaryotic promoter, and a sequence encoding the desired gene product, preceded by an IRES;

b) transfecting a eukaryotic cell culture with the said vector;

c) keeping the stably transfected cells under conditions suitable to promote TIF expression and cell activity; and d) recovering the desired gene product from the said culture.

In another embodiment of the invention, the vector system consists of two recombinant nucleotide vectors. The first vector comprises a sequence encoding a TIF preceded by a weak eukaryotic promoter, and the second vector encodes for the desired gene product preceded by an IRES.

According to this embodiment, the invention is also directed to a method of producing a gene product, said method comprising the steps of:

a) preparing the first recombinant nucleotide vector, comprising a sequence encoding a TIF preceded by a weak eukaryotic promoter that renders the translation of the TIF cap-dependent;

b) preparing a second recombinant vector comprising a sequence encoding the desired gene product, preceded by an IRES;

c) transfecting a eukaryotic cell culture with both said vectors in any convenient order;

d) keeping the stably transfected cells under conditions suitable to promote TIF expression and cell activity; and e) recovering the desired gene product from the said culture.

As stated, the gene product can be any useful material, e.g., a polypeptide or a protein.

Of course, the abovementioned system can include one, two or even more different vectors, which are all introduced into the cell, each vector bearing different genes. For instance the 2A gene and the gene which it is desired to express may be located on two different vectors. Such a union or separation of functions between vectors is also encompassed by the present invention.

In yet another aspect, the invention is directed to a kit for the production of a gene product, said kit containing:

a) A cell line to be transfected.

b) One or more recombinant DNA vectors comprising a TIF preceded by a weak eukaryotic promoter, and an IRES followed by a polyfunctional cloning site into which a desired gene can be inserted.

According to one preferred embodiment of the invention the kit contains:

a) A cell line stably transfected with a recombinant vector containing a TIF preceded by a weak eukaryotic promoter, said cell line constitutively expressing said TIF.

b) A recombinant DNA vector comprising an IRES after which a polyfunctional cloning site is provided.

Thus, the invention provides for easy and convenient means for expressing a protein in high yield. Providing a polyfunctional cloning site after the IRES makes it possible to insert virtually any desired gene into the vector(s) of the invention, and express the said gene in a cell line that constitutively expresses a TIF.

As will be apparent to the skilled person, a great variety of genes encoding TIFs and IRESes as well as promoters and proteins to be expressed, can be provided without exceeding the scope of the invention. Similarly, all recombinant nucleotide vectors which contain a gene encoding a TIF preceded by a weak eukaryotic promoter (in which the TIF is translated in a cap dependent manner) combined with vectors that include an IRES and a gene encoding a polypeptide to be produced (in which the polypeptide is translated in a cap independent manner), and all eukaryotic cells that are transfected with the abovementioned vector(s) are also encompassed by the present invention.

By way of illustration, and without intending to limit the invention in any way, some particular embodiments of the invention will be described hereinafter.

EXAMPLE 1

Expression of AcChoEase

A. Construction of Expression Vectors

Figure 1:
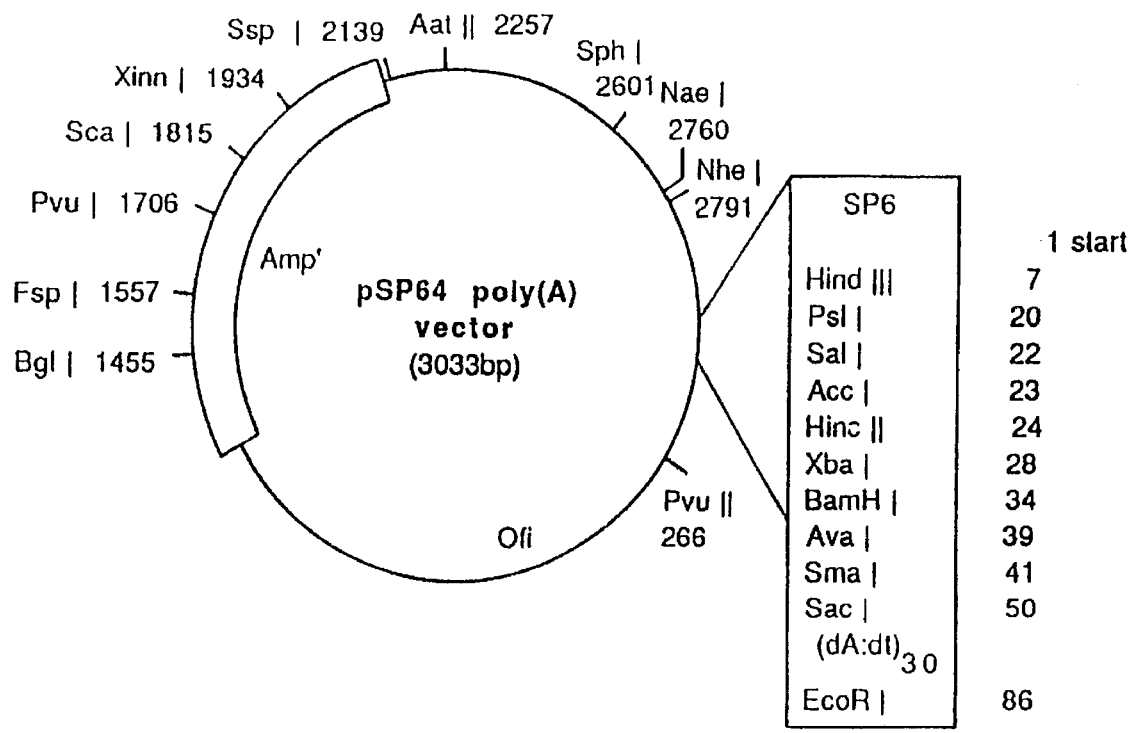
FIG. 1 is the restriction site map of the pSP64 poly (A) vector.
Figure 2:
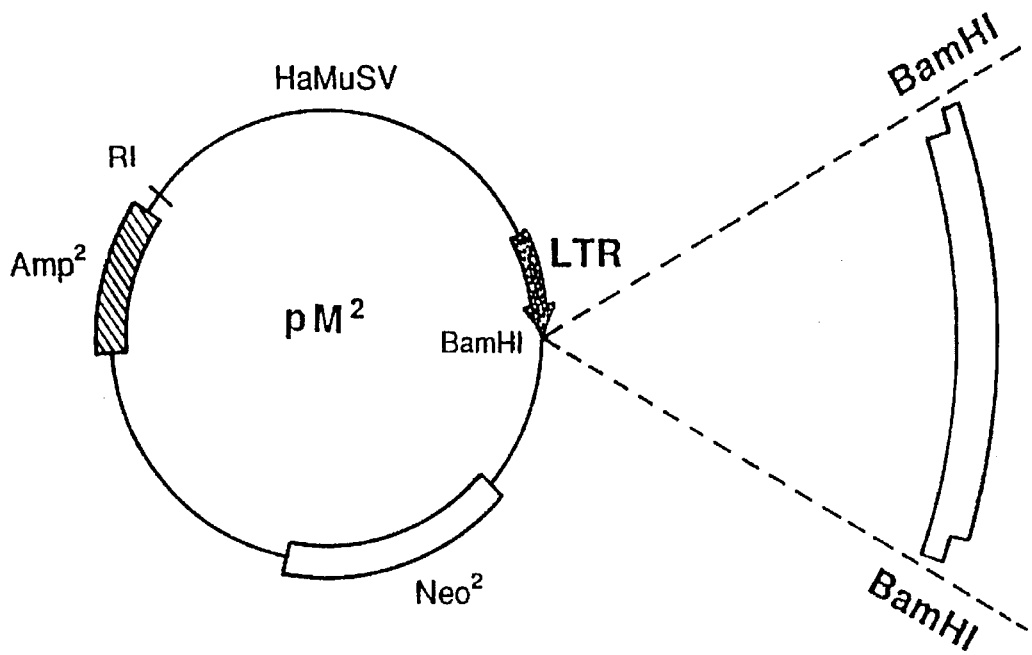
FIG. 2 shows the $PM^2$ plasmid, the BamHI cloning site being enlarged.
Figure 3A:
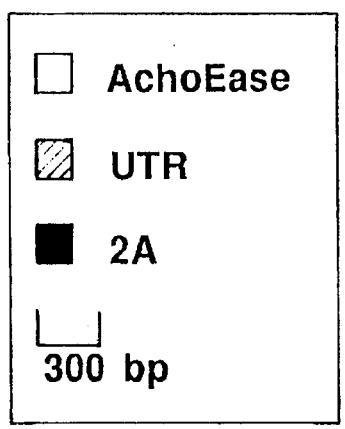
FIGS. 3(a–d) illustrates the engineering of fragments to be inserted into the cloning site of plasmid pSP64.
Figure 3A:
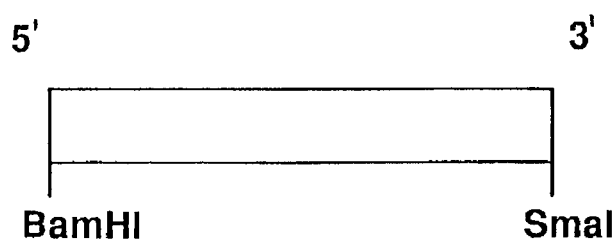
Figure 3B:
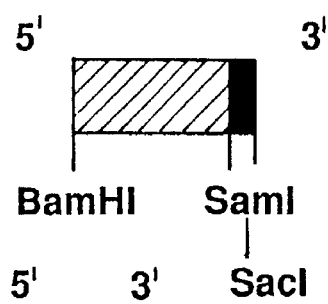
Figure 3C:
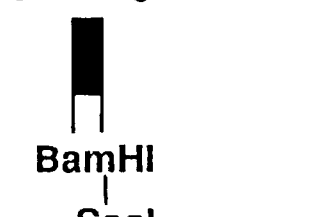
Figure 3D:
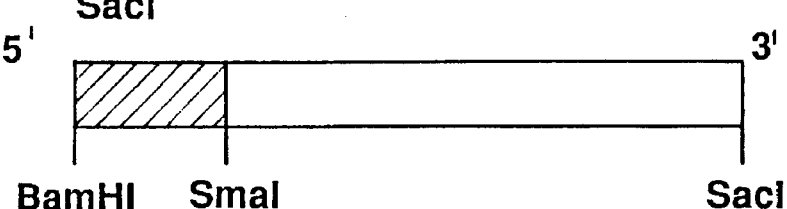

To construct an expression vector for shut-off of the host protein synthesis bearing the sequences of the UTR from BiP or poliovirus cDNA, and 2A domains from poliovirus cDNA, the pSP64 vector (Promega) was used, which contains a poly A sequence in its 3'-terminus (FIG. 1). Additionally, an efficient eukaryotic expression vector, $PM^2$, is used. The $PM^2$ plasmid (FIG. 2) contains the Harvey murine sarcoma virus long terminal repeat (LTR), the bacterial gene (neo), and Amp which confers resistance to Ampicillin antibiotics and can therefore serve as an efficient selection element for creating stable transfected cell lines.

The following constructs were ligated into $PM^2$ at the BamHI cloning site (FIG. 3):

Preparation of Construct 3(a)

For a control-capped reporter gene, the human Acetylcholinesterase (AcChoEase) gene was used. BamHI and SmaI sites were created at codons 1 and 2005 of AcChoEase cDNA, respectively. The fragment BamHI-SmaI was ligated to the pSF64 vector at the cloning site. The EcoRI site at the 3' end was modified into a BamHI site using the Klenow enzyme and a synthetic oligonucleotide linker including the restriction site specific for BamHI digestion. The composite BamHI-BamHI fragment containing the AcChoEase cDNA and poly A was inserted at the BamHI cloning site of $PM^2$.

Preparation of Construct 3(b)

For shut-off of host protein synthesis the plasmid containing polio 5'UTR and the 2A protease coding region was constructed. The expression of 2A protease using this $PM^2$ plasmid was through cap-independent mechanism. BamHI and SmaI sites were created at nucleotides 1 and 698 of poliovirus cDNA, respectively. Additionally, SmaI and SacI sites were created at nucleotides 3380 and 3850, respectively. The two fragments thereof, BamHI-SmaI containing the UTR, and SmaI-SacI which contains the 2A domain, were ligated in frame into the cloning region of the pSP64 vector. The EcoRI site at the 3' end was modified into BamHI site as described above. The composite BamHI-BamHI fragment containing the UTR, 2A and Poly A was inserted at the BamHI cloning site of $PM^2$.

Preparation of Construct 3(c) 2A protease coding region was constructed into $PM^2$. The expression of 2A protease using this plasmid was through cap-dependent mechanism. Expression of 2A protease through this mechanism results in shut-off of host protein synthesis, including the 2A protease. BamHI and SacI sites were created at nucleotides 3380 and 3850, respectively. The BamHI-SacI fragment containing the coding sequence of 2A protease was ligated into the cloning site of the pSP64 vector. The EcoRI site at the 3' end was modified into the BamHI site as described above. The composite BamHI-BamHI fragment containing the 2A protease and poly A was inserted at the BamHI cloning site of $PM^2$.

Preparation of Construct 3(d)

For an uncapped reporter, the UTR sequence was linked to the AcChoEase coding region. BamHI-SmaI sites were created at codons 1 and 698 of poliovirus cDNA, respectively. Additionally, SmaI and SacI were created at codons 1 and 2005 of AcChoEase cDNA. The two fragments BamHI-SmaI containing the UTR and SmaI-SmaI which contain the AcChoEase were ligated in frame into the cloning site of the pSP64 vector. The EcoRI site at the 3' end was modified into BamHI site as described above. The composite BamHI-BamHI fragment containing the UTR, AcChoEase and poly A was ligated at the BamHI cloning site of PM2.

Figure 4A:
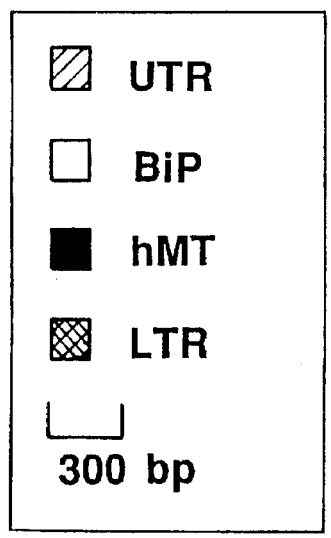
FIGS. 4(a and b) illustrates the construction of the UTR and the BiP coding sequence, and the insertion of the enhanced domain from hMT into the $PM^2$ vector.
Figure 4A:
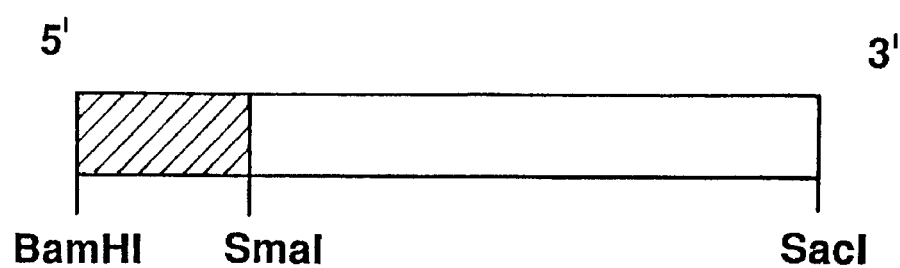
Figure 4B:
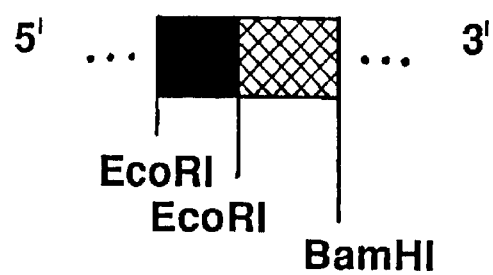

Two additional plasmids were constructed as described hereinafter (FIG. 4):

Preparation of Construct 4(a)

A plasmid containing the UTR and BiP coding sequence was constructed. BamHI and SmaI sites were created at nucleotides 1 and 698 of poliovirus cDNA, respectively. Additionally, SmaI and SacI sites were created at nucleotides 57 and 592 of BiP cDNA, respectively. The two fragments thereof, BamHI-SmaI containing the UTR, and SmaI-SacI containing BiP coding sequence, were ligated in frame into the cloning region of the pSP64 vector. The EcoRI site at the 3' end was modified into BamHI site as described above, and the composite BamHI-BamHI fragment containing UTR, BiP and poly A was inserted into the BamHI cloning of $PM^2$.

Preparation of Construct 4(b)

To enforce an external control by adding metal ions to the condition medium, the enhancer domain from the metallothionein gene was inserted into $PM^2$ Construct 3(b), which contains the polio 5'UTR and the 2A protease. EcoRI sites were created at codons 1 and −300 of the metallothionein gene. The fragment EcoRI-EcoRI which contains the metallothionein control region was rigated into the EcoRI site of $PM^2$ at the first codon.

B. Transfection and Clone Selection

The plasmids were transfected into the Chinese Hamster Ovary cell line (CHO) using the calcium-phosphate method as described previously [DeFeo, D. et al., Proc. Natl. Acad. si. U.S.A., 78, 3504 (1981)]. The cells were maintained in medium I (Ham's F-12 medium supplemented with penicillin (100 units/ml), streptomycin (100 mg/µl) and glutamine (2 mM) containing 5% (v/v) of fetal calf serum at 37° C. in a humidified 5% $CO_2$ incubator). Since the expression vector contains the neomycin resistance gene, transfected cells were selected by growing in culture medium containing 0.25 mg/ml of the neomycin analog G418.

The above constructs were employed for the following transfections:

1) Transfection of AcChoEase under the control of the LTR promoter (Construct 3(a)). The expression of AcChoEase in this transfection was through a cap-dependent mechanism and was used as a control for the other transfections.

2) Co-transfection of the capped AcChoEase (Construct 3(a)) together with the uncapped (cap-independent) UTR-2A (Construct 3(b)). This transformation leads to the inhibition of all cell proteins synthesis through cap-dependent mechanism, including AcChoEase.

3) Co-transfection of the uncapped UTR-AcChoEase (Construct 3(d)) together with the capped 2A (Construct 3(c)). The on-off translation of 2A protease by this transfection was through cap-dependent mechanism. However, translation of AcChoEase was through the uncapped mechanism.

4) Co-transfection of the UTR-AcChoEase (Construct 3(d)) and 5'UTR 2A (construct 3(b)). Expression and translation of 2A protease through cap-independent mechanism stopped protein synthesis of the host cells continuously, except for the translation of AcChoEase which was through cap-independent mechanism.

5) For uncapped expression together with BiP expression, transfection of UTR-BiP coding sequence (Construct 4(a)) was employed together with Constructs 3(d) and 3(b), all at one transfection.

6) In order to enforce an external control of expression, plasmids containing the enhancer domain of metallothionein gene (Construct 4(b)) were co-transfected together with Construct 3(d) (uncapped reporter). The transcription of the cDNAs was modulated by adding metals, such as zinc or copper, to the culture media.

C. Metabolic Labelling

On day 0 transfected cells were placed into 12-well dishes (300,000 cells/well) in 1 ml of medium I (penicillin 100 µg/ml, streptomycin 100 µg/ml, glutamine 2 mM, Ham's F12 medium) supplemented with 5% (v/v) fetal calf serum. On day 1, and for continuous labelling experiments, cells were washed twice with cysteine-free medium II (medium I supplemented with 5% dialyzed calf serum) and labelled for 7 hours in 1 ml of cysteine-free medium II containing 50 µCi/ml [$^{35}$S] cysteine (>1000 Ci/mmol, Amersham Corp.).

D. Immunoprecipitation and Gel Electrophoresis

Medium was collected and chilled on ice. Stock buffer and detergent solutions were added so the final samples contained: 50 mM Tris-HCl (pH 7.8), 150 mM NaCl, 5 mM EDTA, 0.5% (vol/vol) Triton X-100, 0.1% NaDodSO$_4$, phenylmethyl-sulfonyl fluoride (0.3 mg/ml) and iodoacetamid (0.3 mg/ml).

Cell lysates were washed twice with phosphate buffer saline (4° C.) and lysed by adding 0.2 ml of lysis buffer [50 mM Tris, pH 7.8, 150 mM NaCl, 5 mM EDTA and 0.6% (wt/vol) NaDodSO$_4$]. The lysates were diluted with 0.8 ml of dilution buffer (same as lysis buffer, except 0.6% Triton X-100 was substituted for NaDodSO$_4$), and phenylmethyl-sulfonyl fluoride and iodoacetamide were added to a final concentration of 0.3 mg/ml.

The medium and lysate samples were precleared with normal rabbit serum (>1 hr.) and pansorbin (1 hr.) before the samples were immunoprecipitated. Polyclonal antisera were added to lysate and media and incubated overnight at 4° C., as described [Laemmli, U. K., Nature 227, 680 (1970)]. The lysate and media immunoprecipitates were resolved on 15% SDS-polyacrylamide gels as described [Bonneau, A. M., and Sonenberg, N., J. Biol. Chem., 262, 11136 (1987)].

E. Gel Electrophoresis and Peptide Maps

Autoradiography of the immunoprecipitation electrophoresis of the product showed that AcChoEase was produced under regular capped translation (transfection 1), and that uncapped internal translation shutoff conditions prevented the production of AcChoEase protein (transfection 2).

Quantitation by densitometry of AcChoEase proteins from transfections (3), (4) and (1) indicated that internal translations (3) and (4) produced 7 times as much AcChoEase proteins as the normal translation control (1). Transfection (5) (uncapped with BiP) gave results similar to transfections (3) and (4).

Immunoprecipitation electrophoresis of transfection 6 (external control) was performed and compared with transfection 2 (shut-off condition) and with transfection 1 (control).

Quantitation by densitometry of AcChoEase protein indicated that transfection 6 produced 8 times more protein than transfection 1 (control). However, the external control transfection 6 enabled to prolong the lifetime of the infected cell.

F. Spectrophotometric Protein Detection

For studying the amount of expression and the biological activity of the reporter gene, AcChoEase medium was collected from the cell cultures. Before the collection of the media, cells were preincubated for 12 hours with medium which did not contain G418 and FCS, which might interfere with the bioassay. Medium was collected every 24 hours, clarified by centrifugation, and stored at −20° C. until it was assayed for activity.

Expression of AcChoEase was spectrophotometrically detected by Ellman's method [G. L. Ellman et al., Biochem. Pharm., 7, 88 (1961)] for acetylthiocholine hydrolysis. 10 µl of sample were preincubated for 30–45 minutes in individual wells of a 96 well microtiter plate with Ellman's reagent (100 mM phosphate buffer, pH 7.0, 0.5 mM 5-5' dithiobis-2 nitrobenzoic acid, DTNB). The reaction was initiated by addition of 10 µl butyrylthiocholine (20% stock). Hydrolysis of substrate releases free acid and thiocholine. Thiocholine reacts at a molar ratio of 1:1 with DTNB to generate the yellow anion 5-thio-2-nitro-benzoic acid whose high extinction coefficient (E405=13600M-1–cm-1) renders this assay highly sensitive (path length approximately 0.5 cm). The kinetics of substrate hydrolysis was monitored by the Vmax automated microtiter plate reader (Molecular Devices Corp., USA) linked to IBM compatible computer equipped with specially adapted software for the calculation of rate constants. This assay accurately detects cholinesterase activities at nanomole levels of substrate.

Figure 5:
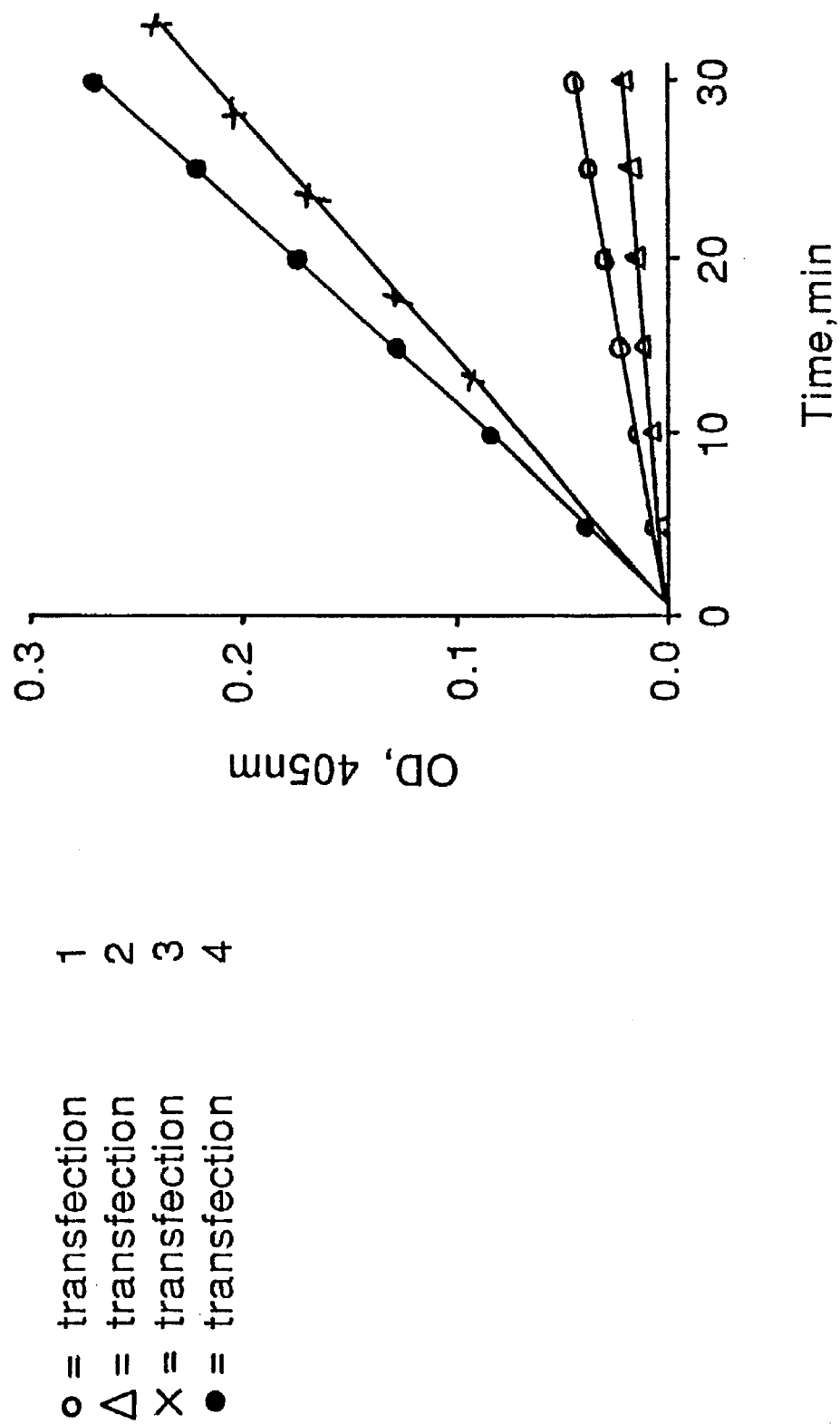
FIG. 5 represents the activity following addition of acetylthiocholine substrate by the Ellman test (Example 1)

FIG. 5 represents the average of three experiments and clearly indicates the increased production of AcChoEase protein in transfections 3 and 4 (internal translation mechanism coupled with shutoff translation of host cell proteins), compared to control transfection 1 (capped translation) and shut-off conditions—Transfection 2.

EXAMPLE 2

Expression of Luciferase

A. Construction of expression vectors

The same procedure as in Example 1 was employed, but instead of using the reporter gene Acetylcholinesterase, the reporter gene containing the cDNA of the firefly Lucfferase was used. The cDNA of the Luciferase gene LC5'1811bp (J. R. Wet et al., Mol. Cell. Biol. (1987) 7, 725–737) was inserted into various constructs in PM$^2$ plasmid through BamHI as cloning site described in Example 1.

B. DNA Transfections

Plasmid DNAs were transfected into CHO cells as described in Example 1. Plasmid DNA (10 µg) was used to transfect each 10 cm plate of cells, each plate containing approximately 10$^6$ CHO cells. Cells were harvested 48 hours after transfection.

C. Luciferase assays

Each plate of transfected cells was washed three times in phosphate buffer, and cells were harvested by extraction buffer (100 mM potassium phosphate (pH 7.8), 1 mM dithiothreidol). The cells (1–5×10$^6$) from each plate were pelleted and resuspended in 100 ml of extraction buffer.

Cells were lysed by three cycles of freezing on dry ice and thawing at 37° C. Cells debris were pelleted by centrifugation at 4° C. A 10 ml sample of extract was added to 350 ml of 25 mM of glycolglycine (pH 7.8) containing 5 mM ATP and 15 mM MgSO$_4$ in a small test tube. The tube was placed in an LKB luminometer equipped with recorder, and the reaction was initiated by the injection of 100 µl of 1 mM luciferin. The enzyme catalyzed a rapid, ATP dependent oxidation of the substrate, which then emitted light at a rate proportional to the amount of luciferase present.

Figure 6:
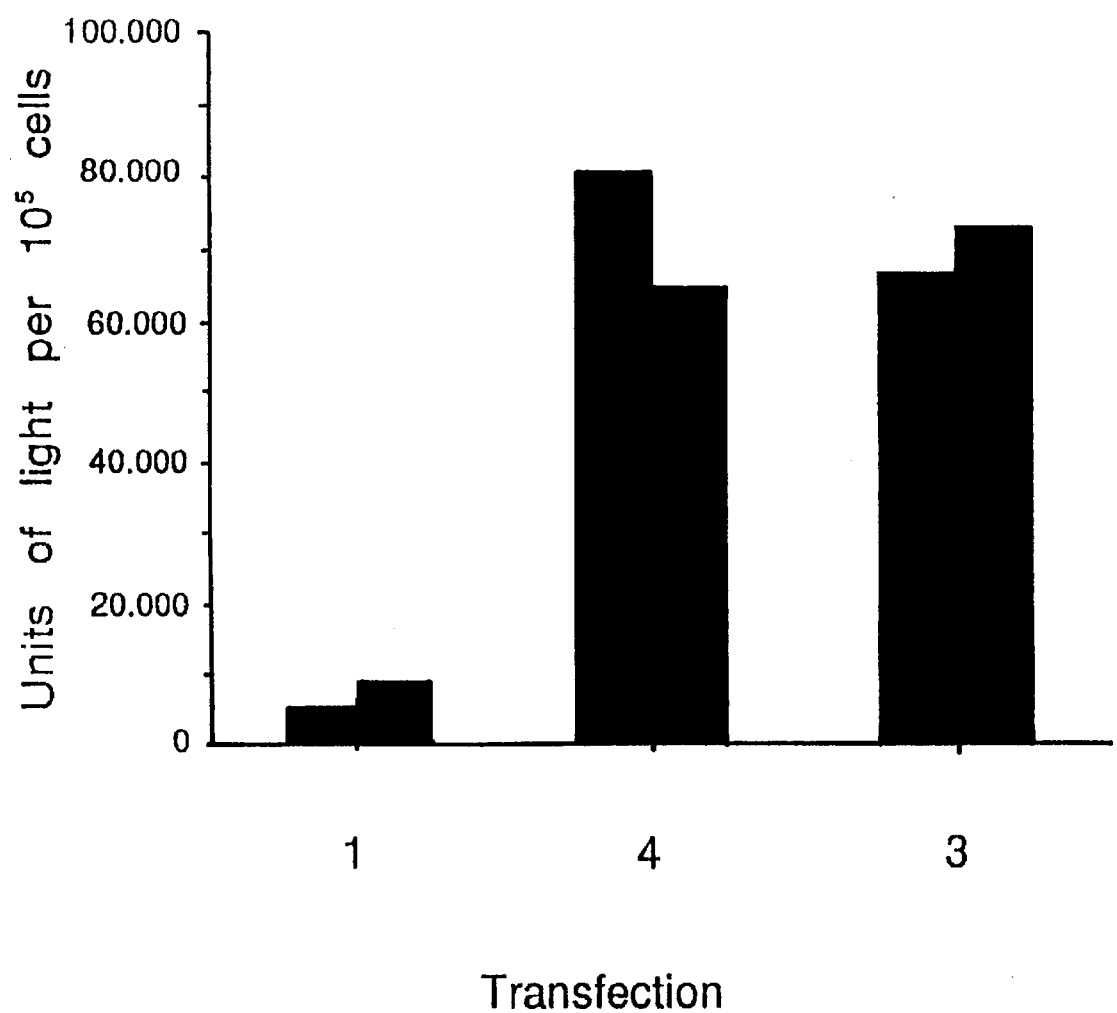
FIG. 6 shows luciferase activities from extracts of Chinese Hamster Ovary (CHO) cells (Example 2)
Figure 7A:
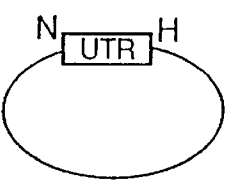
FIG. 7 (panels 1–14) schematically illustrates the constructs of Examples 3 and 4.
Figure 7H:
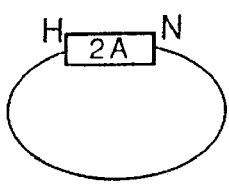
Figure 7B:
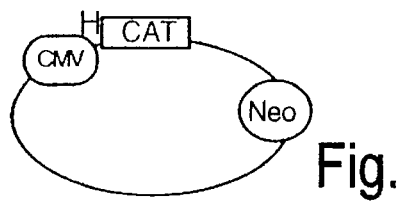
Figure 7I:
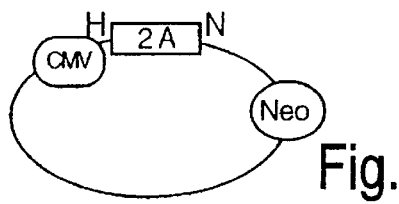
Figure 7C:
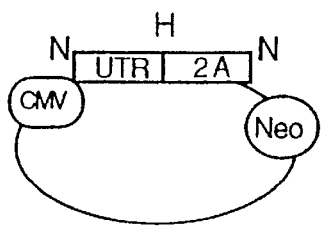
Figure 7J:
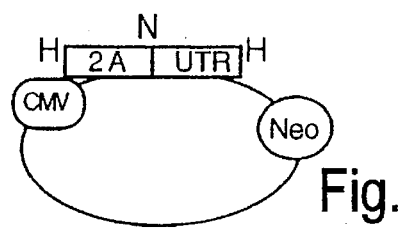
Figure 7D:
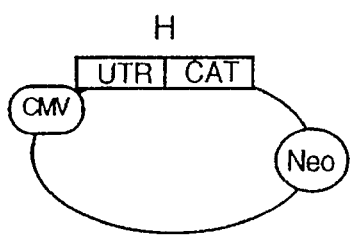
Figure 7K:
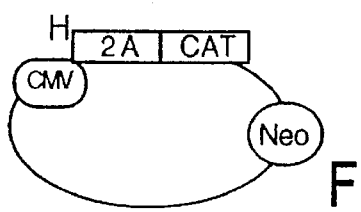
Figure 7E:
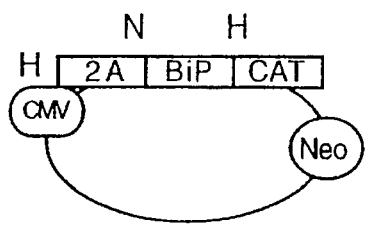
Figure 7L:
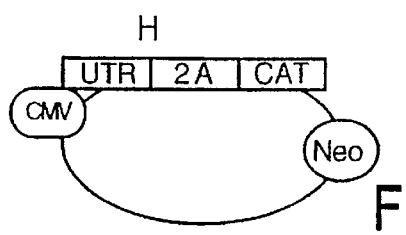
Figure 7F:
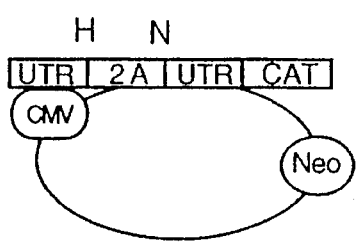
Figure 7M:
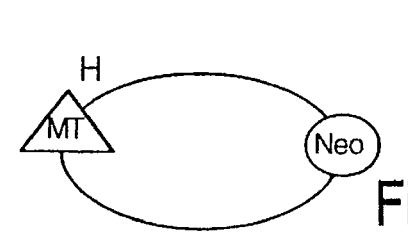
Figure 7G:
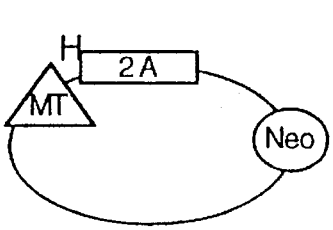
Figure 7N:
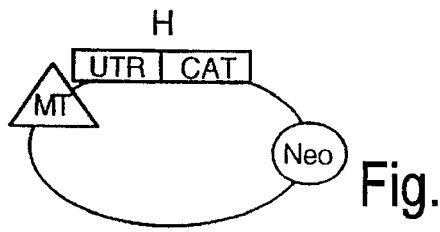

Luciferase activity obtained from extracts of CHO cells transfected with various constructs (as in Example 1) is shown in FIG. 6. Two separate experiments are shown. Transfection 3 and 4 produced 7 to 9 times more luciferase protein compared to control transfection 1.

EXAMPLE 3

Expression of CAT

A. Vector construction

Two stages of cloning are needed in order to obtain the desired constructs. In the first step the genes of choice (the 5'-UTR of the BiP gene and the poliovirus 2A protease) were amplified. The amplified fragments were cloned into the plasmid TA cloning vector of Invitrogen, which enables easy cloning of PCR amplified DNA. In the second stage of the cloning the amplified gene was transferred into the commercial pRc/CMV vector (of Invitrogen). This vector is based on the pUC 19 backbone and carries the strong CMV promoter, the T7 and Sp6 promoters for in vitro RNA synthesis, the SV40 polyadenylation signal, and the Neomycin and bLactamase genes for selection in bacteria (Amp) in mammalian (G418) cells. The cloning and recloning steps were performed by adding to the oligonucleotide primers restriction sites which are present in the polylinker of the vector but not in the genes of choice.

1) Cloning of the 5'-UTR of BiP (UTR)

The following primers were used for amplifying cellular DNA by PCR:

a) 5'-AACATCGCGGCCGCAGGTCGACGCCGGCC AAGACA-3' (Nuc. 372-392 of BiP+NotI site; SEQ ID NO. 6)

b) 5'-CATACGAAGCTTCTTGCCAGCCAGTTCGG CAGC-3' (Nuc. 592-572 of BiP+HindIII site; SEQ ID NO. 7).

The 247 bp amplified band was cloned into the plasmid using the TA cloning kit of Invitrogen (plasmid 1 in FIG. 7).

2) Cloning of the poliovirus 2A protease cDNA from the poliovirus RNA was prepared using the 18-mer primer 5'-ATTTGCTGGGTGAATCCA-3' (Nuc. 3890–3873; SEQ ID NO. 8; Racaniello, V. R. and Baltimore D. Proc. Natl. Acad. Sci. USA 1981, 78, 4887–81).

The 2A protease gene was amplified by PCR from the cDNA using the primers:

a) 5'-TCCAACAAGCTTATGGGTTTTGGCCACCA AAAT (Nuc. 3382–3399+ATG codon and HindIII site; SEQ ID NO. 9; Racaniello, V. R. and Baltimore D. Proc. Natl. Acad. Sci. USA 1981, 78, 4887–81); and b) 5'CCTATCGCGGCCGCTTATTACTGCTCCATA GCCTCCTC-3' (Nuc. 3828–3811+two stop codons and NotI site; SEQ ID NO. 10; Racaniello, V. R. and Baltimore D. Proc. Natl. Acad. Sci. USA 1981, 78, 4887–81).

The 482 bp amplified band was cloned as before (plasmid 2 in FIG. 7).

3) Recloning of the CAT gene

The CAT gene was cut out from the pCAT basic plasmid of Promega (cat. #E1041) and was recloned into the HindIII site of the pRc/CMV plasmid of Invitrogen (plasmid 3 in FIG. 7). This plasmid carries the CMV promoter and the Neomycin (Neo) gene and was used as the reference plasmid for CAT activity in the transfected cells.

4) Cloning of combined constructs

Plasmids 1, 2 and 3 (FIG. 7) were used in the subsequent construction of plasmids 4 to 11 by means known to the skilled person. As an example, after propagating the plasmids in bacteria the BiP insert was isolated (from plasmid 1) using HindIII and NotI, and the CAT plasmid (plasmid 3) was linearized using HindIII. The HindIII site of the BiP insert was ligated (HindIII-HindIII) to the CAT gene; subsequently, the remaining free ends were blunt-ended and self-ligated. The result of these manipulations was plasmid 7 (UTR-CAT). HindIII ligation of the UTR fragment to 2A (plasmid 4) created plasmid 5, and NotI ligation of the same 2 DNAs gave plasmid 6. Since the 2A and the UTR genes are flanked by HindIII and NotI sites, construction of plasmids 8 to 11 took place in a way similar to that described above. Plasmids 3 to 11 therefore contained the following elements:

a) CMV-5'-CAT-3' (The CAT gene under CMV promoter; the above-mentioned plasmid 3)—FIG. 7.

b) CMV-5'-2A-3' (The 2A gene under CMV promoter; plasmid 4 in FIG. 7. This plasmid is the basic plasmid for the 2A protease expression).

c) CMV-5'-UTR-2A-3' (The 2A gene with the 5'-UTR under the CMV promoter; plasmid 5 in FIG. 7, a control for plasmid 4).

d) CMV-5'-2A-UTR-3' (Plasmid 6 in FIG. 7, needed as a control for the 2A activity and for the construction of dicistronic plasmids).

e) CMV-5'-UTR-CAT-3' (The CAT with 5'-UTR of the BiP; plasmid 7 in FIG. 7. This is the basic CAT plasmid for this experiment).

The following dicistronic plasmids were cloned, as well:

f) CMV-5'-2A-CAT (plasmid 8)—FIG. 7.

g) CMV-5'-2A-UTR-CAT-3' (plasmid 9)—FIG. 7.

h) CMV-5'-UTR-2A-CAT-3' (plasmid 10)—FIG. 7.

i) CMV-5'-UTR-2A-UTR-CAT-3' (plasmid 11)—FIG. 7.

The dicistronic plasmids provided positive and negative controls for transfection and expression efficiency under different conditions.

All the above-mentioned plasmids carry the CMV promoter, the Neomycin and b-lactamase genes (for selection in mammalian and bacterial cells), the reporter gene (CAT) with or without the 5'-UTR of the BiP, the poliovirus 2A protease, and combinations of the three DNA segments (genes).

B. Cell transfections

Hela cells were transfected by electrophoration with each of the plasmids and with combinations of plasmids carrying the reporter gene (CAT) and the 2A gene.

C. Assay of CAT Activity

After transfection, cell lysates were analyzed in order to estimate the quantities and stability of the mRNAs by Northern blots and hybridization. The quantities and efficiency of the CAT protein production were assayed as described in "C. N. Gorman et al., Mol. Cell Biol., 2, 1044 (1982)".

The cell extracts were incubated with radioactive chloroamphenicol and acetyl CoA. Acylated Chloroamphenicol was separated from the non-acetylated form by thin layer chromatography followed by autoradiography. CAT activity was determined as intensity at the origin position of unacetylated CAT and monoacetylated CAT products. The CAT activity resulting fi-om the transfection of plasmids (7+5), (7+4), (9) and (11) varied between 500–800% of the activity detected in the transfection of plasmid (3) (control normal eukaryotic translation).

EXAMPLE 4

Cloning of the MT-IIA Promoter

Example 3 was repeated, but the CMV promoter of the pRc/CMV vector was replaced by the inducible metallothionein (MT-IIA) promoter, to create a construct that can be induced to express the 2A protease under externally controlled conditions.

The MT-IIA promoter was amplified by using the following two primers:

a) 5'-ACCATTCGCGACACGGCGGAGGCGCAC GGC-3' (Nuc. 1–20 of MT-IIA+NruI site; SEQ ID NO. 11); and b) 5'-CCTAGGAAGCTTGATCATGGCGAGCTGA AGAGGC-3' (Nuc. 377–356 of MT-IIA+HindIII site; SEQ ID NO. 12)

This amplification yielded a 399 bp long fragment (377 bp of the MT-IIA promoter and two restriction sites) which were digested by the two abovementioned enzyme to create a 384 bp long fragment which was cloned into the NruI/HindIII sites of the pRc/CMV plasmid.

The CMV promoter was removed from the pRc/CMV plasmid by digesting the plasmid with the NruI and HindIII restriction enzymes, thereby removing an insert of 686 bp (Nuc. 206 to 891 on the plasmid) that includes the CMV and the T7 promoters, but left intact the multicloning site. After cloning, the amplified MT-IIA promoter insert into the resulting linearized plasmid is the only promoter active in this construct (plasmid 12, FIG. 7).

The HindIII/NotI 2A protease segment from plasmid 2 (FIG. 7) was cloned into the HindIII of plasmid 12 thus crating plasmid 13 (FIG. 7) which carries the 2A gene under the control of the MT-IIA promoter. Plasmid 14 (FIG. 7) was cloned in two stages: first, the NotI/HindIII UTR insert from plasmid 1 was cloned into the HimdIII site of plasmid 12 (conserving the HindIII site but not the NotI site) and subsequently the CAT gene was cloned into the remaining HindIII site.

Cell transfections and tests were carried out as in Example 3 and comparable CAT activities were obtained when copper ions were added.

EXAMPLE 5

Construction of plasmids Mini TK-2A and ins-2A.

Cloning of 2A

Poliomyelitis virus (Mahoney strain) was grown in HeLa cells. Total vital RNA was extracted from virus particles using Tri Reagent (Molecular Research Center, Inc.) according to the manufacturer instructions. The RNA was reversed PCR using the oligo 5'-CTCTATGTAATTGGTGATTGCC-3' as the first primer and primers $A_1$ (SEQ ID NO. 13) and $A_2$ (SEQ ID NO. 14) encompassing nucleotides 3386–3832 of the RNA (Racaniello, V. R. and Baltimore D. Proc. Natl. Acad. Sci. USA 1981, 78, 4887–81) for amplifcation of the 2A protease ($2A^{pro}$) sequences.

The amplified segment was cloned into BlueScript plasmid (Stratagene Cloning System) using the BamHI and HindIII restriction sites. Using the PCR amplification, restriction sites, as well as an ATG and two stop codons were introduced at the 5' and 3' ends of the protease gene, respectively. The $2A^{pro}$ cDNA was recloned into the specific expression plasmids to create the miniTK-2A the Ins-2A and the CMV-2A constructs. These plasmids were inserted into E. coli and deposited in the Agricultural Research Service (ARS) Patent Culture Collection, Peoria Ill., U.S.A.: plasmid miniTK-2A was inserted into E coli DH5αminiTK-2A and deposited having Accession Number B-21383; plasmid Ins-2A was inserted into E coli DH5αIns-2A and deposited having Accession Number B-21384; plasmid CMV-2A was inserted into E coli DH5αCMV-2A and deposited having Accession Number B-21385.

miniTK-2A Construct

Figure 8:
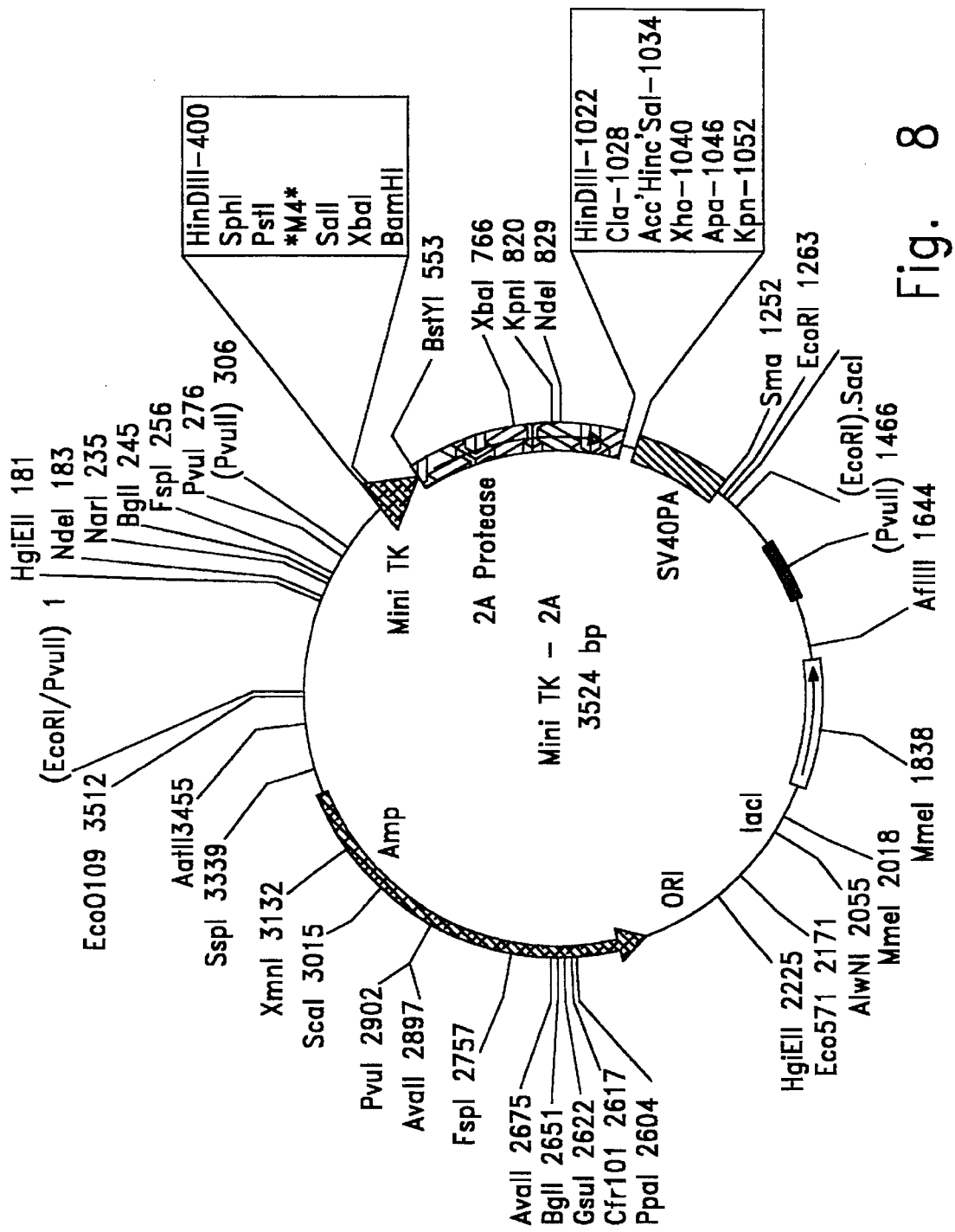
FIG. 8 is the restriction site map of the Mini TK-2A plasmid.

MiniTK promoter was made following Nyborg, J. K. et al. (J. Biol. Chem., 1990, 265, 8237). The promoter fragment was cloned into pUC19 vector (Invitrogen) using the BamHI and BglII restriction sites. A schematic illustration of the miniTK-2A construct is shown in FIG. 8.

Ins-2A Construct

Figure 9:
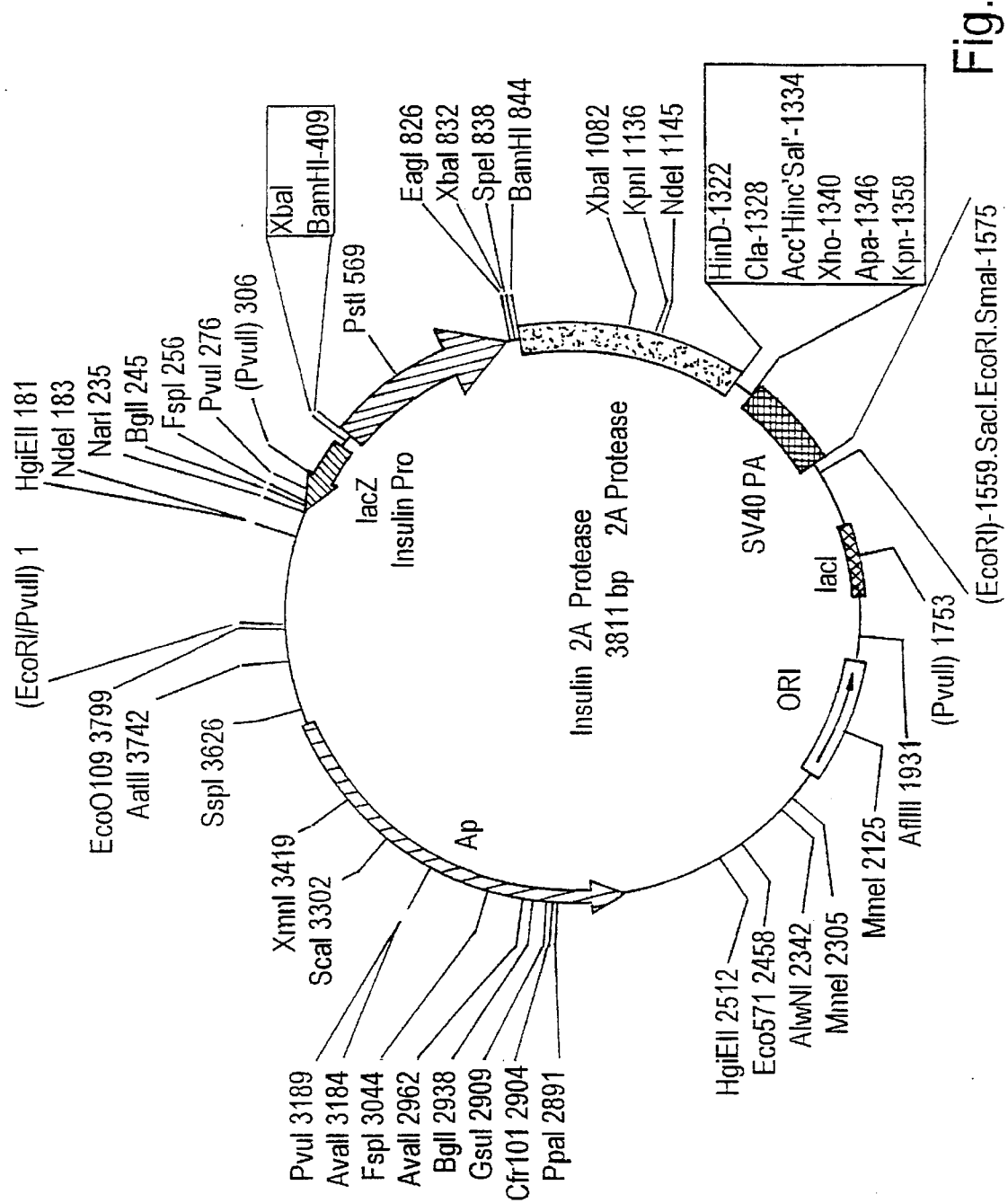
FIG. 9 is the restriction site map of the Insulin-2A plasmid.

The insulin promoter was cloned according to Karlson, O. et. al. (Proc. Natl. Acad. Sci., 1987, 84, 8819). A schematic illustration of the Ins-2A construct is represented in FIG. 9.

EXAMPLE 6

Construction of plasmid pGEH

The pGEH plasmid was constructed by inserting the EMCV 5'-UTR (nucleotides 260–863; Duke et al. J. Virol. 1992, 66, 1602–1609) in front of the cDNA of the human hepatic growth factor (hHGF; Miyazawa, K. et al. Biochem. Biophys. Res. Commun. 1989, 163, 967–973). The vector carries also a strong promoter of cytomegalovirus (CMV), β-globin intron and SV40 polyadenylation site.

Cloning of EMCV's 5'-UTR

The 5'-untranslated region (5'-UTR) of the Encephalomyelitis virus (EMCV) (nucleotides 260–863; Duke et al. J. Virol. 1992, 66, 1602–1609) was PCR cloned from the pCITE plasmid (Novagene) using primers $E_1$ (SEQ ID NO. 15) and $E_2$ (SEQ ID NO. 16).

Figure 10:
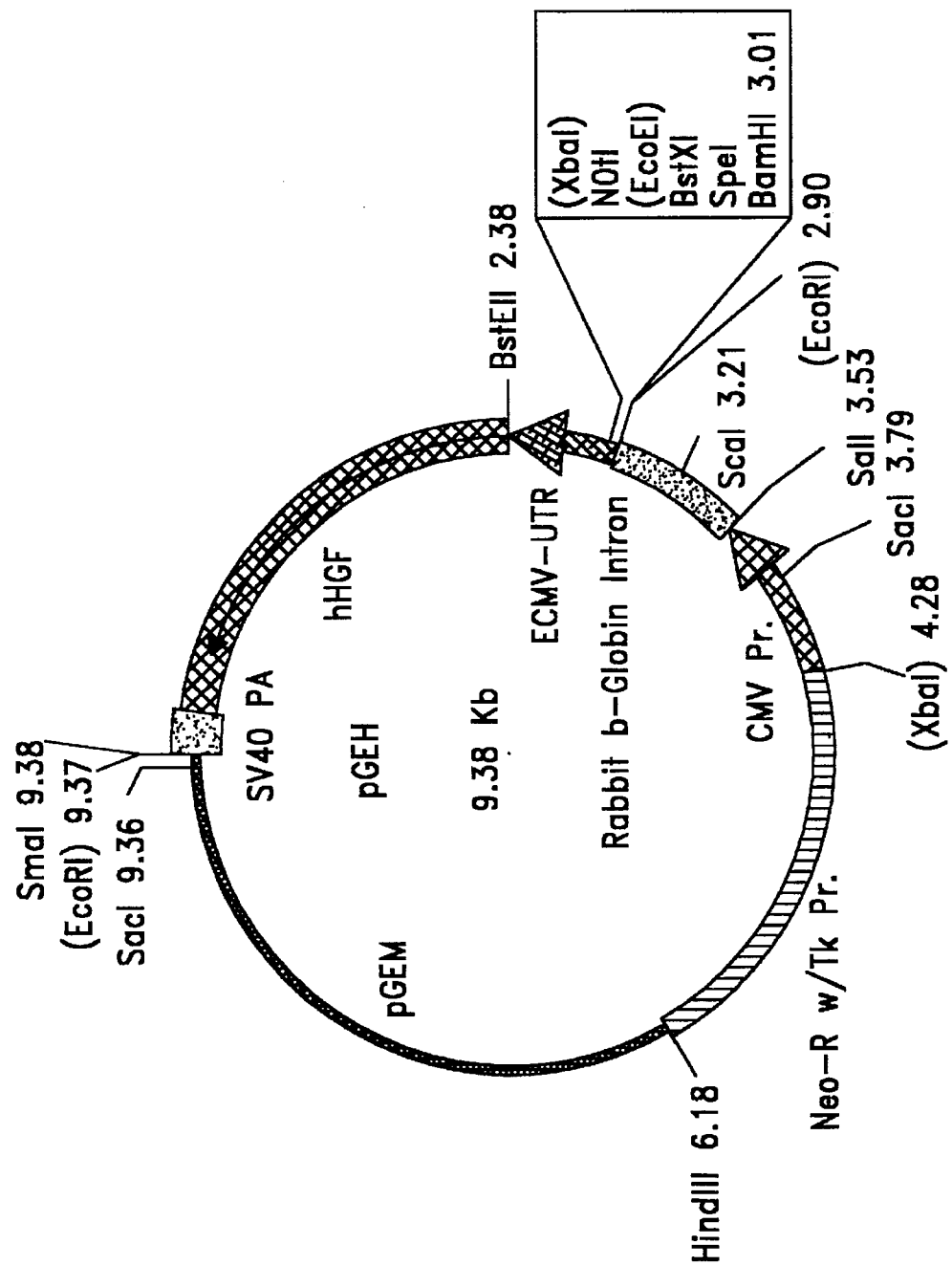
FIG. 10 is the restriction site map of the pGEH plasmid.

The $E_1$ has a NotI restriction site at its 5' and $E_2$ carries an ATG signal and BstEII restriction site in order to enable easy cloning and coordinate insertion of the amplified fragment in the final construct. The PCR amplified 5'-UTR fragment was digested with NotI and BstEII and inserted in front of the hHGF cDNA, originally cloned in the pG1 plasmid. The construct was termed pGEH. A schematic representation of pGEH is shown in FIG. 10.

EXAMPLE 7

Transfection and clone selection

CHO cells (ATCC were suspen) were electrotransfected with pGEH. $5 \times 10^5$ cells were suspended in 800 μl DMEM supplemented with 10% fetal calf serum (FCS), and incubated for 1 minute at room temperature with 10 μg of purified plasmid DNA prior to the electrotransfection. EASYJECT+electroporator (EquiBio) was used in twin pulse mode. The electrical pulse parameters were: 650 volts, 25 μF and 99 Ohms for the first pulse and 100 volts, 1500 μF and 99 Ohms for the second pulse, and inter pulse time was 0.1 second.

Stable clones, expressing the Neo resistance gene (G418) were selected by growth in DMEN medium containing 10% fetal calf serum and 800 μg/ml G418. Individual clones were picked up and were analyzed for the level of hHGF production.

Clone No. 1202 was retransfected with either (Hygromycin) or miniTK-2A+Hygromycin. The electrotransfection conditions were as described above.

The transfected cells were grown under Neo+Hygro selection as described above. A dozen colonies were picked up at random. Clones No. 4321 and 4340 were selected for further experiments.

EXAMPLE 8

Enhancement of hHGF expression in CHO cells
Assay for hHGF expression 50,000 cells/well were seeded in 12 well plates with 1.5 ml medium containing 10% fetal calf serum (FCS) and 300 μg/ml G418 and/or 150 μg/ml Hygromycin. The medium was changed 24 hours later (day 0), and every second day afterwards. 100 μl of the culture medium were taken for ELISA assay. Measurements were made in duplicates. A sensitive enzyme linked immunosorbent assay (ELISA) was used utilizing hHGF specific mono- and polyclonal antibodies (Ab's) via a sandwich technique. Briefly, anti-hHGF monoclonal Ab's were adsorbed to 96 well plates by incubation of the plates overnight at 4° C. with 50 μl solution of 25 μg/ml of the Ab's in PBS. The plates were washed with PBS and then incubated for 2 hours at 37° C. with the blocking solution (1% BSA, 0.02% $NaH_2$, and 0.05% Tween 20 in PBS). Tested samples were applied in aliquots of 50 μl/well. The plates were then incubated overnight at 4° C., rinsed 3 times with PBS supplemented with 0.05% Tween 20 (washing solution) and then rabbit polyclonal antiserum against hHGF diluted 1:1000 in blocking solution was added to the wells. After further incubation for two hours at room temperature, the plates were rinsed again and incubated for two hours with alkaline phosphatase-conjugated purified sheep anti-rabbit IgG. The assay was developed using phosphatase substrate (Sigma). The enzymatic product was measured calorimetrically at 405 nm. Pure hHGF was used as a standard.

A. 2A effect in CHO cells.

The influence of $2A^{pro}$ on protein translation via a cap-independent mechanism was evaluated by analyzing hHGF production in CHO cells stably transformed with pGEH. The pGEH construct harbors an hHGF cDNA preceded by the internal ribosomal entry site (IRES) of the EMCV. CHO cells were electrotransfected with pGEH plasmid DNA and stable colonies were isolated as described in example 7. The best hHGF-producing clone (clone C1202) was retransfected either with the Hygromycin plasmid or with the mini TK-2A plasmid together with the Hygromycin plasmid (in a ratio of 1:10). Stable clones resistant to Hygromycin were isolated.

Figure 12:
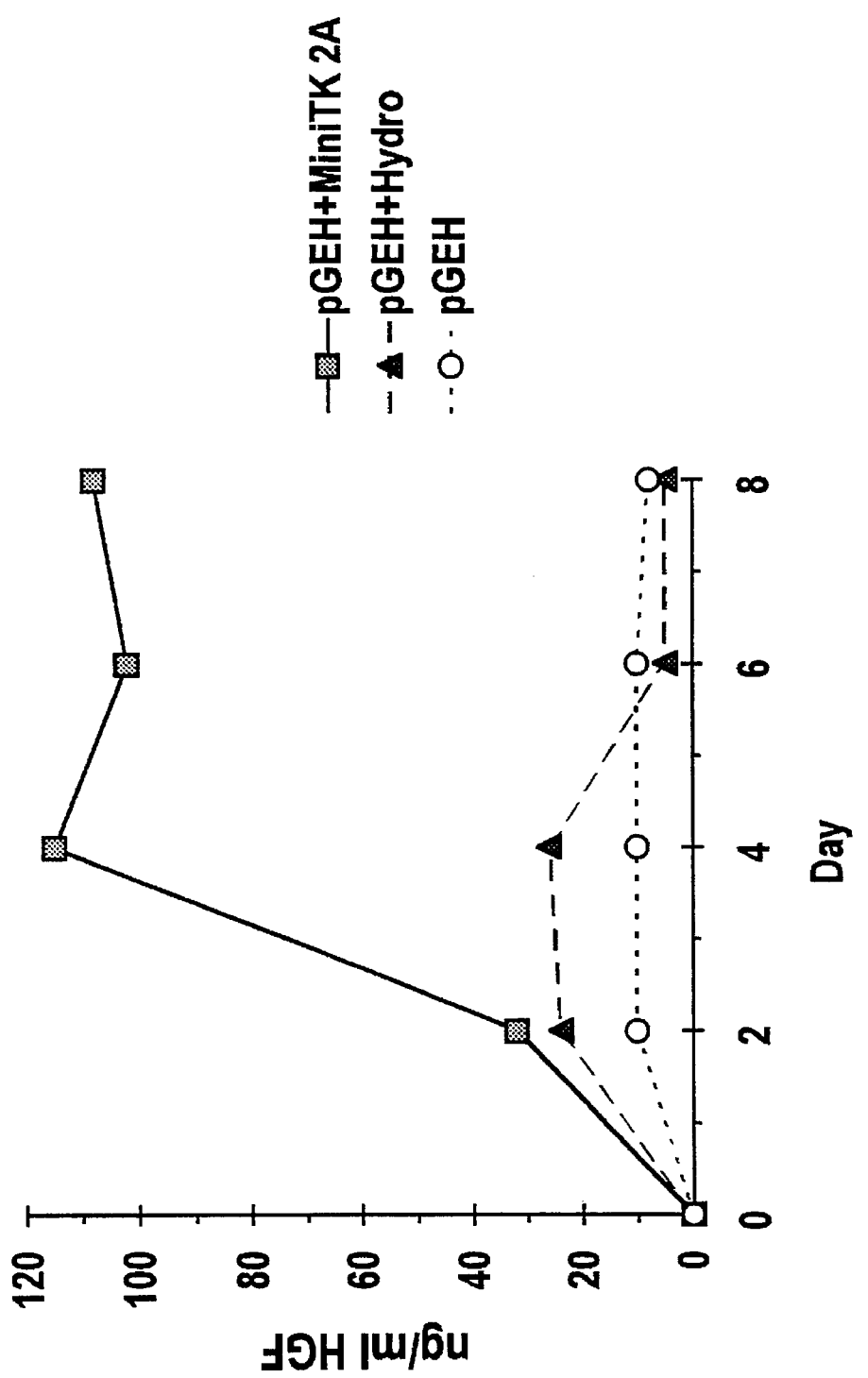
FIG. 12 describes the effect of plasmid Mini TK-2A on the enhancement of hHGF expression in transfected CHO cells.

Three clones were selected for the expression experiment: the original clone which carried the pGEH construct (clone C1202), and two clones that were derived from it by the retransfection procedure. Clone C4321 carries $2A^{pro}$ and Hygromycin in addition to the hHGF cDNA and clone No. C4340 harbors only the Hygromycin plasmid. The cells were seeded in wells and the samples for hHGF measurements were collected as was described. As shown in FIG. 12, the amount of hHGF production in cells carrying $2A^{pro}$ was significantly greater as compared to the amount produced by cells carrying the pGEH construct alone (with or without the Hygromycin plasmid).

B. 2A-Effect in RK-13 cells.

Figure 11:
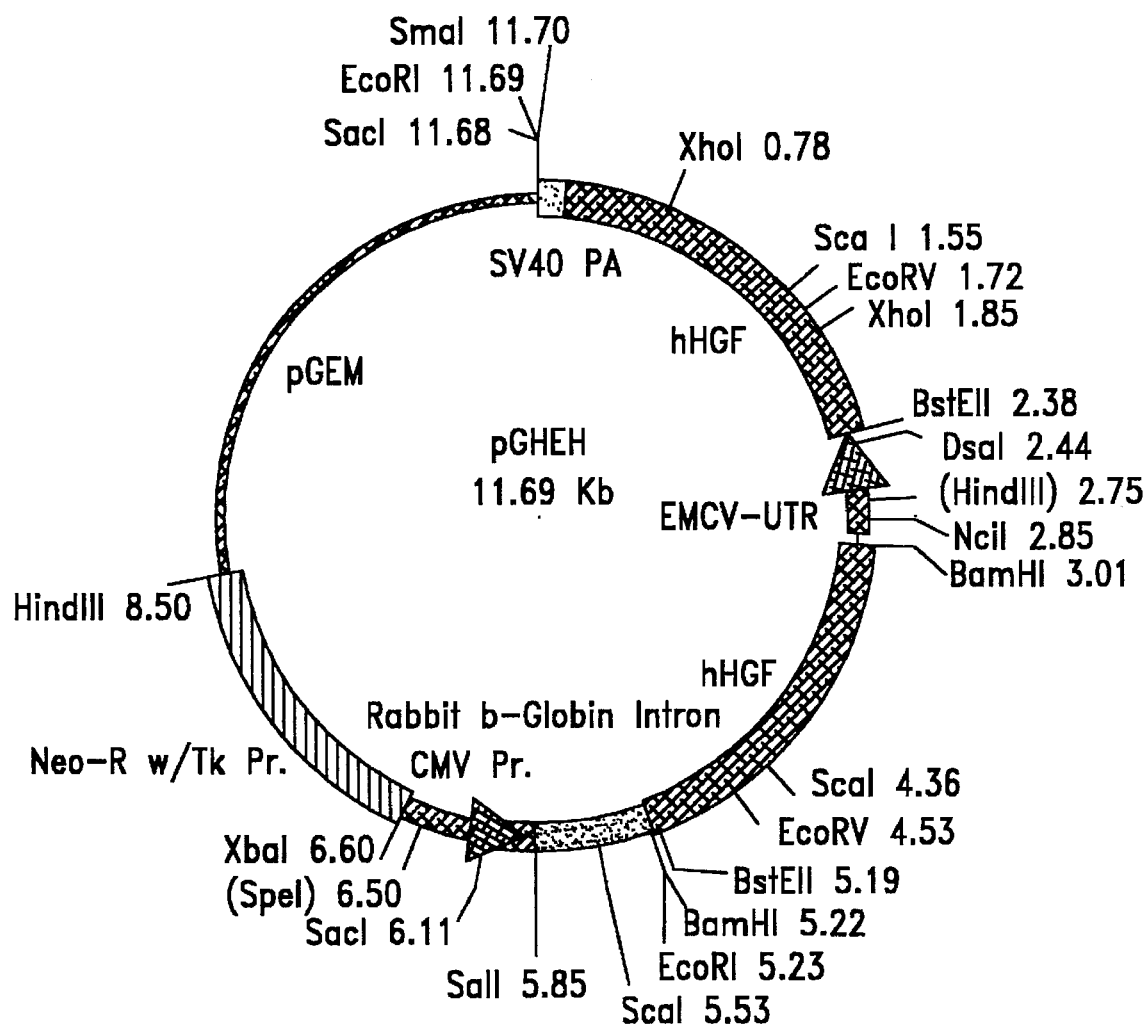
FIG. 11 is the restriction site map of the di-cistronic pGHEH plasmid.
Figure 13:
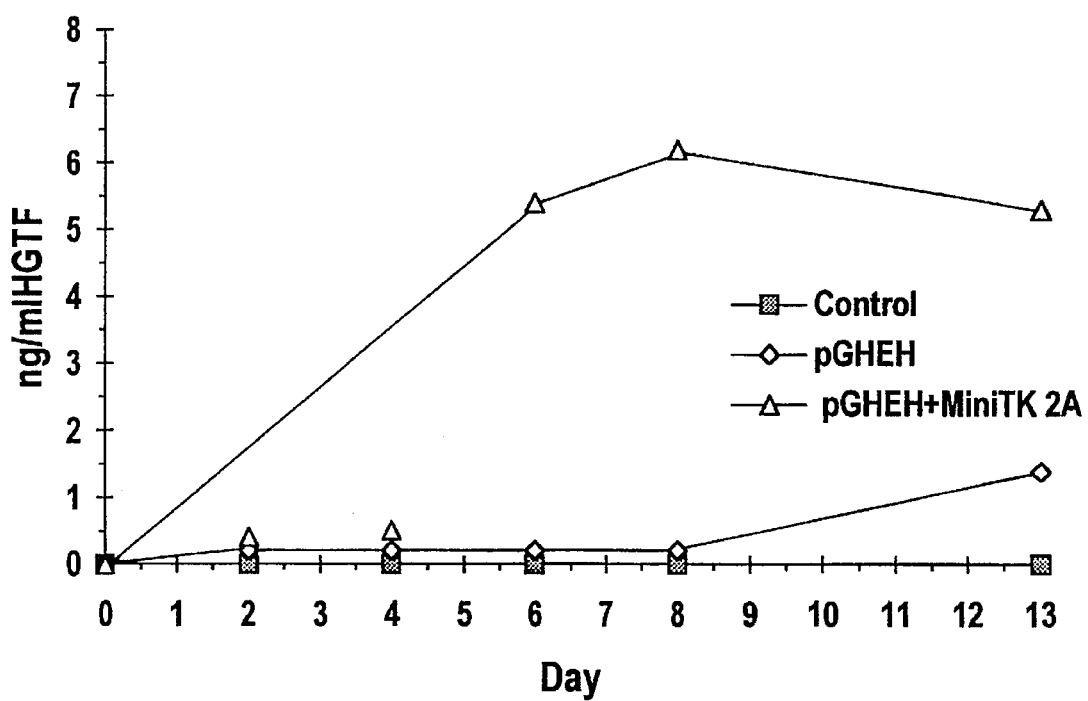
FIG. 13 describes the effect of plasmid Mini TK-2A on the enhancement of hHGF expression in RK-13 cells transfected with the di-cistronic pGHEH plasmid.

The effect of the combination of the di-cistronic construct pGHEH (FIG. 11) and plasmid mini TK-2A was examined on rabbit RK-13 cells (FIG. 13). The experiment had two goals: (1) to demonstrate that the method is applicable for various mammalian cell lines; and (2) to demonstrate the efficiency of the di-cistronic construct pGHEH in combination with the 2A protein. pGHEH construct harbors two hHGF cDNA genes separated by the EMCV IRES while the first hHGF cDNA is preceded by the strong CMV promoter. This construct produces di-cistronic mRNA in which the first gene is translated via cap-dependent mechanism while the second is translated via cap-independent mechanism. RK-13 cells (ATCC CCL37) were electrotransfected with pGHEH plasmid DNA and clones were selected and then retransfected with Mini TK-2A as described in part A above. FIG. 13 demonstrates the elevation of expression when the RK-13 cells were retransfected with Mini TK-2A. hHGF production in the presence of Mini TK-2A when the constructs contained in the IRES is greatly enhanced. The effect of Mini TK-2A in stable cell lines from the mouse c127 cells and monkey SV80 cells is observed as well.

The above description and examples have been provided for the purpose of illustration and are not intended to limit the invention in any way. As will be understood by the stilled person, the invention can be exploited with different vectors, cell-lines, end products and purposes. The invention is not meant, therefore, to be limited to any specific cell, cell line, vector, TIF, IRES or protein, and a large variety of applications can be devised, without exceeding the scope of the invention or departing from its spirit.

---

We claim:

1. A recombinant DNA vector or vector system collectively comprising:
   a) a gene encoding a translation initiation factor (TIF) of a eukaryotic translation factor (ETF), preceded by a promoter, wherein the promoter is a weak eukaryotic promoter, wherein the weak eukaryotic promoter is Mini TK or insulin promoter; and
   b) at least one internal ribosome entry site (IRES) region, followed by a cloning site into which at least one gene encoding a polypeptide to be produced can be inserted.

2. A recombinant DNA vector or vector system according to claim 1, wherein the ETF is endogenous eIF-4F.

3. A recombinant DNA vector or vector system according to claim 1, wherein the TIF is a viral gene product.

4. A recombinant DNA vector or vector system according to claim 1, wherein the TIF is the poliovirus 2A protease.

5. A recombinant DNA vector or vector system according to claim 1, wherein the IRES is any viral or eukaryotic IRES.

6. A recombinant DNA vector or vector system according to claim 5, wherein the IRES is the untranslated region (UTR) of a picornavirus or the UTR of human immunoglobulin heavy chain-binding protein (BiP).

7. A recombinant DNA vector or vector system according to claim 1, collectively comprising: 1) a gene encoding a TIF of an eukaryotic translation factor (ETF), preceded by a weak eukaryotic promoter; and 2) at least one internal ribosome entry site (IRES) region, followed by a polyfunctional cloning site.

8. A recombinant DNA vector or vector system according to claim 1, collectively comprising: 1) a gene encoding a TIF of an eukaryotic translation factor (ETF), preceded by a weak eukaryotic promoter; and 2) at least one internal ribosome entry site (IRES) region, followed by at least one gene encoding a polypeptide.

9. A recombinant DNA vector system according to claim 1 wherein the system comprises two vectors, the first vector containing a gene encoding a TIF of a eukaryotic translation factor (ETF), preceded by a weak eukaryotic promoter, and the second vector containing at least one internal ribosome entry site (IRES) region, followed by at least one gene encoding a polypeptide.

10. A recombinant DNA vector system according to claim 1 wherein the system comprises of more than two vectors.

11. A recombinant DNA vector system according to claim 9, wherein the first vector is plasmid Mini TK-2A or Ins-2A.

12. A recombinant DNA vector system according to claim 9, wherein the second vector is plasmid pGEH.

13. A recombinant DNA vector or vector system according to claim 1, wherein the expressed protein is human hepatic growth factor.

14. A plasmid selected from the group consisting of: Mini TK-2A, Ins-2A, CMV-2A and pGEH.

15. An $E.$ $coli$ strain selected from the group consisting of: DH5αminiTK-2A having accession number NRRL B-21383; DH5αIns-2A having accession number NRRL B-21384; and DH5αCMV-2A having accession number NRRL B-21385.

16. A plasmid pGHEH.

17. A stable mammalian cell line that contains the vector Mini TK-2A.

18. A stable mammalian cell line that contains the vectors Mini TK-2A or pGEH.

19. A stable mammalian cell line that contains the vectors Mini TK-2A or pGHEH.

20. A method for producing gene products comprising:
   a) Providing a recombinant nucleotide vector or vector system according to claim 1;
   b) Inserting one or more genes to be expressed into the said vector or vector system;
   c) stably transfecting a cell line with the said vector or vector system;
   d) keeping the transfected cell line under conditions suitable to promote gene expression; and
   e) recovering the desired gene product from the said cell line.

21. A method for the in vitro production of a gene product, comprising the steps of:
   a) preparing one or more recombinant DNA vector or vector system of claim 1;
   b) transfecting a eukaryotic cell culture with the said vector;
   c) keeping the transfected cell culture under conditions suitable to promote cell activity; and
   d) recovering the desired gene product from the said culture.

22. A method for the in vitro production of a gene product, comprising the steps of:
   a) preparing a first recombinant nucleotide vector, comprising a sequence encoding a TIF, preceded by a eukaryotic cap-dependent promoter, wherein the eukaryotic cap-dependent promoter is Mini TK or insulin promoter;
   b) preparing a second recombinant nucleotide vector, comprising at least a sequence encoding the desired gene product, preceded by an IRES;
   c) transfecting a eukaryotic cell culture with both the said first vector and the said second vector;
   d) keeping the transfected cell culture under conditions suitable to promote cell activity; and
   e) recovering the desired gene product from the said culture.

23. A method for the extracellular production of a gene product, comprising the steps of:
   a) preparing a medium containing a recombinant nucleotide vector or vector system comprising:
      (i) a gene encoding a translation initiation factor (TIF) of a eukaryotic translation factor (ETF), preceded by a promoter, wherein the promoter is a weak eukaryotic promoter, wherein the weak eukaryotic promoter is Mini TK or insulin promoter; and
      (ii) at least one internal ribosome entry site (IRES) region, followed by a cloning site into which at least one gene encoding a polypeptide to be produced can be inserted, wherein (i) and (ii) may occur on the same or separate vectors;
   b) providing in the medium substrates, ribosomes and promotors required for effecting translation;
   c) keeping the medium under conditions suitable to promote gene expression; and
   d) recovering the desired gene product from the said medium.

24. A stable mammalian cell line that contains a vector or vectors according to claim 1.

25. A stable mammalian cell line that contains a vector or vectors according to claim 14.

26. A stable mammalian cell line that contains a vector or vectors according to claim 15.

27. A lyophilized mammalian cell line that contains a vector or vectors according to claim 1.

28. A lyophilized mammalian cell line that contains a vector or vectors according to claim 14.

29. A lyophilized mammalian cell line that contains a vector or vectors according to claim 15.

30. A lyophilized mammalian cell line that contains a vector or vectors according to claim 16.

31. A lyophilized mammalian cell line according to claim 17.

32. A lyophilized mammalian cell line according to claim 18.

33. A kit comprising a vector or vector system according to claim 1.

34. A kit according to claim 33 including a cell line according to claim 16.

35. A kit according to claim 33 including a cell line according to claim 17.

36. A kit according to claim 33 including a cell line according to claim 18.

37. A kit according to claim 33 including a cell line according to claim 19.

38. A method according to claim 21, further comprising providing for external activation of the TIF expression.

39. A method according to claim 22, further comprising providing for external activation of the TIF expression.

40. A method according to claim 21, wherein the gene product is a polypeptide.

41. A method according to claim 22, wherein the gene product is a polypeptide.

42. A method according to claim 21, wherein the gene product is a protein.

43. A method according to claim 22, wherein the gene product is a protein.

44. A method according to claim 38, wherein the external activation of TIF expression is mediated by metallothionein activity.

45. A method according to claim 39, wherein the external activation of TIF expression is mediated by metallothionein activity.

* * * * *